United States Patent
Layman et al.

(10) Patent No.: US 7,914,467 B2
(45) Date of Patent: Mar. 29, 2011

(54) TUBULAR MEMBER HAVING TAPERED TRANSITION FOR USE IN A MEDICAL DEVICE

(75) Inventors: Ted W. Layman, Park City, UT (US); Clay W. Northrop, Salt Lake City, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 704 days.

(21) Appl. No.: 11/836,039

(22) Filed: Aug. 8, 2007

(65) Prior Publication Data

US 2007/0287955 A1 Dec. 13, 2007

Related U.S. Application Data

(63) Continuation-in-part of application No. 10/604,504, filed on Jul. 25, 2003.

(60) Provisional application No. 60/399,046, filed on Jul. 25, 2002.

(51) Int. Cl.
*A61B 5/00* (2006.01)
*A61M 25/00* (2006.01)

(52) U.S. Cl. ...................................... 600/585

(58) Field of Classification Search .......... 600/585
See application file for complete search history.

(56) References Cited

U.S. PATENT DOCUMENTS

| | | | |
|---|---|---|---|
| 1,553,227 A | 9/1925 | Feyk et al. | |
| 1,866,888 A | 7/1932 | Hawley | |
| 2,275,827 A | 3/1942 | Plensler | |
| 2,413,805 A | 1/1947 | Vickers | |
| 2,441,166 A | 5/1948 | Raspert | |
| 2,561,890 A | 7/1951 | Stoddard | |
| 2,722,614 A | 11/1955 | Fryklund | |
| 2,857,536 A | 10/1958 | Light | |
| 2,864,017 A | 12/1958 | Waltscheff | |
| 2,871,793 A | 2/1959 | Michie et al. | |
| 3,249,776 A | 5/1966 | Anderson et al. | |
| 3,322,984 A | 5/1967 | Anderson | |
| 3,334,253 A | 8/1967 | Hill | |
| 3,363,470 A | 1/1968 | Yavne | |
| 3,452,227 A | 6/1969 | Welch | |
| 3,452,742 A | 7/1969 | Muller | |

(Continued)

FOREIGN PATENT DOCUMENTS

AU 723040 12/1997

(Continued)

OTHER PUBLICATIONS

"Mechanical Design and Systems Handbook", H.A. Rothbart, 1964, p. 33-13 (one sheet).

*Primary Examiner* — Max Hindenberg
*Assistant Examiner* — Brian Szmal
(74) *Attorney, Agent, or Firm* — Seager, Tufte & Wickhem, LLC

(57) ABSTRACT

An elongated medical device and components therefore, and methods for making and using the same. An example embodiment includes an elongated metallic tubular member including a tapered transition region disposed between two sections having different physical characteristics, such as flexibility characteristics. In some cases, the tubular member includes a section including a plurality of slots formed therein. Some example embodiments include a medical device including such a tubular member.

31 Claims, 11 Drawing Sheets

U.S. PATENT DOCUMENTS

| | | | |
|---|---|---|---|
| 3,463,953 A | 8/1969 | Maxwell | |
| 3,512,019 A | 5/1970 | Durand | |
| 3,544,868 A | 12/1970 | Bates | |
| 3,625,200 A | 12/1971 | Muller | |
| 3,686,990 A | 8/1972 | Margolien | |
| 3,841,308 A | 10/1974 | Tate | |
| 3,890,977 A | 6/1975 | Wilson | |
| 3,906,938 A | 9/1975 | Fleischhacker | |
| 4,000,672 A | 1/1977 | Sitterer et al. | |
| 4,003,369 A | 1/1977 | Heilman et al. | |
| 4,020,829 A | 5/1977 | Willson et al. | |
| 4,142,119 A | 2/1979 | Madey | |
| 4,215,703 A | 8/1980 | Wilson | |
| 4,330,725 A | 5/1982 | Hintz | |
| 4,425,919 A | 1/1984 | Alston, Jr. et al. | |
| 4,476,754 A | 10/1984 | Ducret | |
| 4,482,828 A | 11/1984 | Vergues et al. | |
| 4,545,390 A | 10/1985 | Leary | |
| 4,563,181 A | 1/1986 | Wijayarathna et al. | |
| 4,574,670 A | 3/1986 | Johnson | |
| 4,580,551 A | 4/1986 | Siegmund et al. | |
| 4,583,404 A | 4/1986 | Bernard et al. | |
| 4,635,270 A | 1/1987 | Gürs | |
| 4,665,906 A | 5/1987 | Jervis | |
| 4,676,249 A | 6/1987 | Arenas et al. | |
| 4,721,117 A | 1/1988 | Mar et al. | |
| 4,737,153 A | 4/1988 | Shimamura et al. | |
| 4,763,647 A | 8/1988 | Gambale | |
| 4,774,949 A | 10/1988 | Fogarty | |
| 4,781,092 A | 11/1988 | Gaiser | |
| 4,781,186 A | 11/1988 | Simpson et al. | |
| 4,786,220 A | 11/1988 | Fildes et al. | |
| 4,790,331 A | 12/1988 | Okada et al. | |
| 4,800,890 A | 1/1989 | Cramer | |
| 4,811,743 A | 3/1989 | Stevens | |
| 4,827,941 A | 5/1989 | Taylor et al. | |
| 4,831,858 A | 5/1989 | Yoshizawa | |
| 4,832,047 A | 5/1989 | Sepetka et al. | |
| 4,846,186 A | 7/1989 | Box et al. | |
| 4,846,193 A | 7/1989 | Tremulis et al. | |
| 4,867,173 A | 9/1989 | Leoni | |
| 4,875,489 A | 10/1989 | Messner et al. | |
| 4,884,579 A | 12/1989 | Engelson | |
| 4,911,148 A | 3/1990 | Sosnowski et al. | |
| 4,917,102 A | 4/1990 | Miller et al. | |
| 4,922,164 A | 5/1990 | Jacobsen et al. | |
| 4,922,777 A | 5/1990 | Kawabata | |
| 4,932,959 A | 6/1990 | Horzewski et al. | |
| 4,934,380 A | 6/1990 | Toledo | |
| 4,953,553 A | 9/1990 | Tremulis | |
| 4,954,022 A | 9/1990 | Underwood et al. | |
| 4,955,384 A | 9/1990 | Taylor et al. | |
| 4,955,862 A | 9/1990 | Sepetka | |
| 4,960,410 A | 10/1990 | Pinchuk | |
| 4,964,409 A | 10/1990 | Tremulis | |
| 4,966,163 A | 10/1990 | Kraus et al. | |
| 4,968,306 A | 11/1990 | Huss et al. | |
| 4,985,022 A | 1/1991 | Fearnot et al. | |
| 4,989,608 A | 2/1991 | Ratner | |
| 4,990,143 A | 2/1991 | Sheridan | |
| 4,994,069 A | 2/1991 | Ritchart et al. | |
| 4,998,923 A | 3/1991 | Samson et al. | |
| 5,007,434 A | 4/1991 | Doyle et al. | |
| 5,009,137 A | 4/1991 | Dannatt | |
| 5,040,543 A | 8/1991 | Badera et al. | |
| 5,050,606 A | 9/1991 | Tremulis | |
| 5,052,404 A | 10/1991 | Hodgson | |
| 5,059,177 A | 10/1991 | Towne et al. | |
| 5,063,935 A | 11/1991 | Gamble | |
| 5,065,769 A | 11/1991 | De Toledo | |
| 5,095,915 A | 3/1992 | Engelson | |
| 5,106,455 A | 4/1992 | Jacobsen et al. | |
| 5,109,830 A | 5/1992 | Cho | |
| 5,125,395 A | 6/1992 | Adair | |
| 5,135,531 A | 8/1992 | Shiber | |
| 5,144,959 A | 9/1992 | Gambale et al. | |
| 5,147,317 A | 9/1992 | Shank et al. | |
| 5,181,668 A | 1/1993 | Tsuji et al. | |
| 5,205,830 A | 4/1993 | Dassa et al. | |
| 5,211,183 A | 5/1993 | Wilson | |
| 5,228,441 A | 7/1993 | Lundquist | |
| 5,238,004 A | 8/1993 | Sahatjian et al. | |
| 5,242,759 A | 9/1993 | Hall | |
| 5,243,996 A | 9/1993 | Hall | |
| 5,250,069 A | 10/1993 | Nobuyoshi et al. | |
| 5,254,106 A | 10/1993 | Feaster | |
| 5,254,107 A | 10/1993 | Soltesz | |
| 5,256,144 A | 10/1993 | Kraus et al. | |
| 5,257,974 A | 11/1993 | Cox | |
| 5,259,393 A | 11/1993 | Corso, Jr. et al. | |
| 5,267,979 A | 12/1993 | Appling et al. | |
| 5,267,982 A | 12/1993 | Sylvanowicz | |
| 5,279,562 A | 1/1994 | Sirhan et al. | |
| 5,284,128 A | 2/1994 | Hart | |
| 5,300,032 A | 4/1994 | Hibbs et al. | |
| 5,304,131 A | 4/1994 | Paskar | |
| 5,306,252 A | 4/1994 | Yutori et al. | |
| 5,308,435 A | 5/1994 | Ruggles et al. | |
| 5,315,906 A | 5/1994 | Ferenczi et al. | |
| 5,315,996 A | 5/1994 | Lundquist | |
| 5,318,529 A | 6/1994 | Kontos | |
| 5,322,064 A | 6/1994 | Lundquist | |
| 5,329,923 A | 7/1994 | Lundquist | |
| 5,333,620 A | 8/1994 | Moutafis et al. | |
| 5,334,145 A | 8/1994 | Lundquist et al. | |
| 5,336,205 A | 8/1994 | Zenzen et al. | |
| 5,341,818 A | 8/1994 | Abrams et al. | |
| 5,345,937 A | 9/1994 | Middleman et al. | |
| 5,345,945 A | 9/1994 | Hodgson et al. | |
| 5,354,623 A | 10/1994 | Hall | |
| 5,358,493 A | 10/1994 | Schweich et al. | |
| 5,358,796 A | 10/1994 | Nakamura et al. | |
| 5,365,942 A | 11/1994 | Shank | |
| 5,365,943 A | 11/1994 | Jansen | |
| 5,368,564 A | 11/1994 | Savage | |
| 5,368,661 A | 11/1994 | Nakamura et al. | |
| 5,376,084 A | 12/1994 | Bacich et al. | |
| 5,381,782 A | 1/1995 | DeLaRama et al. | |
| 5,406,960 A | 4/1995 | Corso, Jr. | |
| 5,411,476 A | 5/1995 | Abrams | |
| 5,437,288 A | 8/1995 | Schwartz et al. | |
| 5,438,993 A | 8/1995 | Lynch et al. | |
| 5,439,000 A | 8/1995 | Gunderson et al. | |
| 5,441,483 A | 8/1995 | Avitall | |
| 5,441,489 A | 8/1995 | Utsumi et al. | |
| 5,447,812 A | 9/1995 | Fukuda et al. | |
| 5,454,787 A | 10/1995 | Lundquist | |
| 5,460,187 A | 10/1995 | Daigle et al. | |
| 5,470,330 A | 11/1995 | Goldenberg et al. | |
| 5,476,701 A | 12/1995 | Berger | |
| 5,477,856 A | 12/1995 | Lundquist | |
| 5,496,294 A | 3/1996 | Hergenrother et al. | |
| 5,497,785 A | 3/1996 | Viera | |
| 5,507,301 A | 4/1996 | Wasicek et al. | |
| 5,507,729 A | 4/1996 | Lindenberg et al. | |
| 5,507,751 A | 4/1996 | Goode et al. | |
| 5,507,766 A | 4/1996 | Kugo et al. | |
| 5,514,128 A | 5/1996 | Hillsman et al. | |
| 5,520,194 A | 5/1996 | Miyata et al. | |
| 5,520,645 A | 5/1996 | Imran et al. | |
| 5,531,719 A | 7/1996 | Takahashi | |
| 5,533,985 A | 7/1996 | Wang | |
| 5,546,958 A | 8/1996 | Thorud et al. | |
| 5,551,444 A | 9/1996 | Finlayson | |
| 5,554,139 A | 9/1996 | Okajima | |
| 5,562,619 A | 10/1996 | Mirarchi et al. | |
| 5,569,197 A | 10/1996 | Helmus et al. | |
| 5,569,200 A | 10/1996 | Umeno et al. | |
| 5,569,218 A | 10/1996 | Berg | |
| 5,571,073 A | 11/1996 | Castillo | |
| 5,573,520 A | 11/1996 | Schwartz et al. | |
| 5,584,821 A | 12/1996 | Hobbs et al. | |
| 5,599,326 A | 2/1997 | Carter | |
| 5,599,492 A | 2/1997 | Engelson | |
| 5,601,539 A | 2/1997 | Corso, Jr. | |
| 5,605,162 A | 2/1997 | Mirzaee et al. | |
| 5,622,184 A | 4/1997 | Ashby et al. | |

| | | | | | | |
|---|---|---|---|---|---|---|
| 5,630,806 | A | 5/1997 | Inagaki et al. | 6,228,073 B1 | 5/2001 | Noone et al. |
| 5,637,089 | A | 6/1997 | Abrams et al. | 6,248,082 B1 | 6/2001 | Jafari |
| 5,656,011 | A | 8/1997 | Uihlein et al. | 6,251,092 B1 | 6/2001 | Qin et al. |
| 5,658,264 | A | 8/1997 | Samson et al. | 6,254,549 B1 | 7/2001 | Ramzipoor |
| 5,666,968 | A | 9/1997 | Imran et al. | 6,260,458 B1 | 7/2001 | Jacobsen et al. |
| 5,666,969 | A | 9/1997 | Urick et al. | 6,273,404 B1 | 8/2001 | Holman et al. |
| 5,669,926 | A | 9/1997 | Aust et al. | 6,273,876 B1 | 8/2001 | Klima et al. |
| 5,676,659 | A | 10/1997 | McGurk | 6,273,879 B1 | 8/2001 | Keith et al. |
| 5,676,697 | A | 10/1997 | McDonald | 6,290,656 B1 | 9/2001 | Boyle et al. |
| 5,682,894 | A | 11/1997 | Orr et al. | 6,296,616 B1 | 10/2001 | McMahon |
| 5,690,120 | A | 11/1997 | Jacobsen et al. | 6,296,631 B1 | 10/2001 | Chow |
| 5,720,300 | A | 2/1998 | Fagan et al. | 6,302,870 B1 | 10/2001 | Jacobsen et al. |
| 5,722,609 | A | 3/1998 | Murakami | 6,325,790 B1 | 12/2001 | Trotta |
| 5,728,063 | A | 3/1998 | Preissman et al. | 6,338,725 B1 | 1/2002 | Hermann et al. |
| 5,741,429 | A | 4/1998 | Donadio, III et al. | 6,346,091 B1 | 2/2002 | Jacobsen et al. |
| 5,746,701 | A | 5/1998 | Noone | 6,352,515 B1 | 3/2002 | Anderson et al. |
| 5,769,830 | A | 6/1998 | Parker | 6,355,005 B1 | 3/2002 | Powell et al. |
| 5,772,609 | A | 6/1998 | Nguyen et al. | 6,355,027 B1 | 3/2002 | Le et al. |
| 5,782,809 | A | 7/1998 | Umeno et al. | 6,368,315 B1 | 4/2002 | Gillis et al. |
| 5,788,653 | A | 8/1998 | Lorenzo | 6,368,316 B1 | 4/2002 | Jansen et al. |
| 5,788,654 | A | 8/1998 | Schwager | 6,375,628 B1 | 4/2002 | Zadno-Azizi et al. |
| 5,788,707 | A | 8/1998 | Del Toro et al. | 6,375,774 B1 | 4/2002 | Lunn et al. |
| 5,792,124 | A | 8/1998 | Horrigan et al. | 6,379,369 B1 | 4/2002 | Abrams et al. |
| 5,797,856 | A | 8/1998 | Frisbie et al. | 6,390,993 B1 | 5/2002 | Cornish et al. |
| 5,800,454 | A | 9/1998 | Jacobsen et al. | 6,398,758 B1 | 6/2002 | Jacobsen et al. |
| 5,807,075 | A | 9/1998 | Jacobsen et al. | 6,428,489 B1 | 8/2002 | Jacobsen et al. |
| 5,807,249 | A | 9/1998 | Qin et al. | 6,428,512 B1 | 8/2002 | Anderson et al. |
| 5,810,885 | A | 9/1998 | Zinger | 6,431,039 B1 | 8/2002 | Jacobsen et al. |
| 5,813,996 | A | 9/1998 | St. Germain et al. | 6,440,088 B1 | 8/2002 | Jacobsen |
| 5,827,225 | A | 10/1998 | Schwab | 6,478,778 B1 | 11/2002 | Jacobsen et al. |
| 5,827,242 | A | 10/1998 | Follmer et al. | 6,488,637 B1 | 12/2002 | Eder et al. |
| 5,833,632 | A | 11/1998 | Jacobsen et al. | 6,491,648 B1 | 12/2002 | Cornish et al. |
| 5,836,926 | A | 11/1998 | Peterson et al. | 6,491,671 B1 | 12/2002 | Larson, III et al. |
| 5,843,050 | A | 12/1998 | Jones et al. | 6,503,244 B1 | 1/2003 | Hayman |
| 5,843,244 | A | 12/1998 | Pelton et al. | 6,508,803 B1 | 1/2003 | Horikawa et al. |
| 5,851,203 | A | 12/1998 | van Muiden | 6,524,301 B1 | 2/2003 | Wilson et al. |
| 5,895,378 | A | 4/1999 | Nita | 6,530,934 B1 | 3/2003 | Jacobsen et al. |
| 5,897,537 | A | 4/1999 | Berg et al. | 6,547,779 B2 | 4/2003 | Levine et al. |
| 5,902,254 | A | 5/1999 | Magram | 6,553,880 B2 | 4/2003 | Jacobsen et al. |
| 5,902,290 | A | 5/1999 | Peacock, III et al. | 6,556,873 B1 | 4/2003 | Smits |
| 5,904,657 | A | 5/1999 | Unsworth et al. | 6,579,246 B2 | 6/2003 | Jacobsen et al. |
| 5,906,618 | A | 5/1999 | Larson, III | 6,602,207 B1 | 8/2003 | Mann et al. |
| 5,911,715 | A | 6/1999 | Berg et al. | 6,602,280 B2 | 8/2003 | Chobotov |
| 5,911,717 | A | 6/1999 | Jacobsen et al. | 6,610,046 B1 | 8/2003 | Usami et al. |
| 5,916,177 | A | 6/1999 | Schwager | 6,623,448 B2 | 9/2003 | Slater |
| 5,916,178 | A | 6/1999 | Noone | 6,636,758 B2 | 10/2003 | Sanchez et al. |
| 5,916,194 | A | 6/1999 | Jacobsen et al. | 6,638,266 B2 | 10/2003 | Wilson et al. |
| 5,931,830 | A | 8/1999 | Jacobsen et al. | 6,652,508 B2 | 11/2003 | Griffin et al. |
| 5,935,108 | A | 8/1999 | Katoh et al. | 6,682,493 B2 | 1/2004 | Mirigian |
| 5,947,940 | A | 9/1999 | Beisel | 6,689,120 B1 | 2/2004 | Gerdts |
| 5,951,539 | A | 9/1999 | Nita et al. | 6,702,762 B2 | 3/2004 | Jafari et al. |
| 5,971,975 | A | 10/1999 | Mills et al. | 6,712,826 B2 | 3/2004 | Lui |
| 5,980,471 | A | 11/1999 | Jafari | 6,730,095 B2 | 5/2004 | Olson, Jr. et al. |
| 6,001,068 | A | 12/1999 | Uchino et al. | 6,749,560 B1 | 6/2004 | Konstorum et al. |
| 6,004,279 | A | 12/1999 | Crowley et al. | 6,766,720 B1 | 7/2004 | Jacobsen et al. |
| 6,014,919 | A | 1/2000 | Jacobsen et al. | 6,777,644 B2 | 8/2004 | Peacock, III et al. |
| 6,017,319 | A | 1/2000 | Jacobsen et al. | 6,811,544 B2 | 11/2004 | Schaer |
| 6,022,343 | A | 2/2000 | Johnson et al. | 6,837,898 B2 | 1/2005 | Boyle et al. |
| 6,022,369 | A | 2/2000 | Jacobsen et al. | 6,866,642 B2 | 3/2005 | Kellerman et al. |
| 6,024,730 | A | 2/2000 | Pagan | 6,887,235 B2 | 5/2005 | O'Connor et al. |
| 6,027,461 | A | 2/2000 | Walker et al. | 6,918,882 B2 | 7/2005 | Skujins et al. |
| 6,042,553 | A | 3/2000 | Solar et al. | 6,997,937 B2 | 2/2006 | Jacobsen et al. |
| 6,045,547 | A | 4/2000 | Ren et al. | 7,001,369 B2 | 2/2006 | Griffin et al. |
| 6,048,339 | A | 4/2000 | Zirps et al. | 7,074,197 B2 | 7/2006 | Reynolds et al. |
| 6,056,702 | A | 5/2000 | Lorenzo | 7,153,277 B2 | 12/2006 | Skujins et al. |
| 6,063,101 | A | 5/2000 | Jacobsen et al. | 7,182,735 B2 | 2/2007 | Shireman et al. |
| 6,063,200 | A | 5/2000 | Jacobsen et al. | 7,494,687 B2 * | 2/2009 | Cox .............................. 600/585 |
| 6,066,361 | A | 5/2000 | Jacobsen et al. | 2002/0013540 A1* | 1/2002 | Jacobsen et al. .............. 600/585 |
| 6,106,485 | A | 8/2000 | McMahon | 2002/0019599 A1 | 2/2002 | Rooney et al. |
| 6,106,488 | A | 8/2000 | Fleming et al. | 2003/0009208 A1 | 1/2003 | Snyder et al. |
| 6,139,510 | A | 10/2000 | Palermo | 2003/0060732 A1 | 3/2003 | Jacobsen et al. |
| 6,165,292 | A | 12/2000 | Abrams et al. | 2003/0069522 A1 | 4/2003 | Jacobsen et al. |
| 6,171,296 | B1 | 1/2001 | Chow | 2003/0216668 A1 | 11/2003 | Howland et al. |
| 6,183,410 | B1 | 2/2001 | Jacobsen et al. | 2004/0116831 A1 | 6/2004 | Vrba |
| 6,193,686 | B1 | 2/2001 | Estrada et al. | 2004/0142643 A1 | 7/2004 | Miller et al. |
| 6,197,014 | B1 | 3/2001 | Samson et al. | 2004/0167436 A1 | 8/2004 | Reynolds et al. |
| 6,203,485 | B1 | 3/2001 | Urick | 2004/0167437 A1 | 8/2004 | Sharrow et al. |
| RE37,148 | E | 4/2001 | Shank | 2004/0167441 A1 | 8/2004 | Reynolds et al. |
| 6,214,042 | B1 | 4/2001 | Jacobsen et al. | 2004/0181174 A2 | 9/2004 | Davis et al. |

| | | | | | | |
|---|---|---|---|---|---|---|
| 2004/0181176 | A1 | 9/2004 | Jafari et al. | JP | 6169996 | 6/1994 |
| 2004/0210163 | A1* | 10/2004 | Osawa et al. ............... 600/585 | JP | 6-63224 | 9/1994 |
| 2006/0121218 | A1 | 6/2006 | Obara et al. | JP | 6312313 | 11/1994 |
| 2006/0122537 | A1 | 6/2006 | Reynolds et al. | JP | 728562 | 5/1995 |
| 2006/0189896 | A1 | 8/2006 | Davis et al. | JP | 7124164 | 5/1995 |
| 2006/0264904 | A1 | 11/2006 | Kerby et al. | JP | 7124263 | 5/1995 |
| 2008/0021347 | A1 | 1/2008 | Jacobsen et al. | JP | 7136280 | 5/1995 |
| 2008/0021348 | A1 | 1/2008 | Jacobsen et al. | JP | 7148264 | 6/1995 |
| 2008/0021400 | A1 | 1/2008 | Jacobsen et al. | JP | 7505561 | 6/1995 |
| 2008/0021401 | A1 | 1/2008 | Jacobsen et al. | JP | 7037199 | 7/1995 |
| 2008/0021402 | A1 | 1/2008 | Jacobsen et al. | JP | 7185009 | 7/1995 |
| 2008/0021403 | A1 | 1/2008 | Jacobsen et al. | JP | 7255855 | 10/1995 |
| 2008/0021404 | A1 | 1/2008 | Jacobsen et al. | JP | 7275366 | 10/1995 |
| 2008/0021405 | A1 | 1/2008 | Jacobsen et al. | JP | 751067 | 11/1995 |
| 2008/0021406 | A1 | 1/2008 | Jacobsen et al. | JP | 8-229888 | 9/1996 |
| 2008/0021407 | A1 | 1/2008 | Jacobsen et al. | JP | 8509141 | 10/1996 |
| 2008/0021408 | A1 | 1/2008 | Jacobsen et al. | JP | 8317988 | 12/1996 |
| 2008/0077119 | A1 | 3/2008 | Snyder et al. | JP | 9000164 | 4/1997 |
| | | | | JP | 9-276413 | 10/1997 |

FOREIGN PATENT DOCUMENTS

| | | | | | |
|---|---|---|---|---|---|
| AU | 733966 | 4/1998 | JP | 9276413 | 10/1997 |
| BR | PI 9712829 | 1/2000 | JP | 9-294813 A | 11/1997 |
| CA | 2266685 | 5/2006 | JP | 9294813 | 11/1997 |
| CA | 2255781 | 3/2007 | JP | 10-118193 | 5/1998 |
| CN | 1230914 | 10/1999 | JP | 10328191 | 12/1998 |
| DE | 2539191 | 3/1976 | JP | 11-267224 A | 10/1999 |
| DE | 285514 | 12/1990 | JP | 2000-197704 A | 7/2000 |
| EP | 0 045 931 | 2/1982 | JP | 2000-510722 A | 8/2000 |
| EP | 0 069 522 | 1/1983 | JP | 2000-511083 A | 8/2000 |
| EP | 0 087 933 | 9/1983 | JP | 2001-500808 A | 1/2001 |
| EP | 0 111 044 | 6/1984 | JP | 3325828 | 7/2002 |
| EP | 0 181 174 | 5/1986 | JP | 2002-529137 A | 9/2002 |
| EP | 0 377 453 | 7/1990 | JP | 2002-542901 A | 12/2002 |
| EP | 0 565 065 | 6/1996 | JP | 2002-543896 A | 12/2002 |
| EP | 0 778 038 | 6/1997 | JP | 2003-517893 A | 6/2003 |
| EP | 0 778 039 | 6/1997 | JP | 3649604 | 2/2005 |
| EP | 0 778 040 | 6/1997 | JP | 2005-534407 | 11/2005 |
| EP | 0 812 599 | 12/1997 | SU | 712908 | 1/1980 |
| EP | 0 865 772 | 9/1998 | SU | 758421 | 8/1980 |
| EP | 0 865 773 | 9/1998 | SU | 1529365 | 12/1989 |
| EP | 0 521 595 | 5/1999 | WO | WO 90/02520 | 3/1990 |
| EP | 0 917 885 | 5/1999 | WO | WO 91/13364 | 9/1991 |
| EP | 0 937 481 | 8/1999 | WO | WO 92/04072 | 3/1992 |
| EP | 0 790 066 | 4/2000 | WO | WO 92/07619 | 5/1992 |
| EP | 0 608 853 | 4/2003 | WO | WO 93/04722 | 3/1993 |
| EP | 0 935 947 | 12/2004 | WO | WO 93/11313 | 6/1993 |
| EP | 0 934 141 | 11/2005 | WO | WO 95/24236 | 9/1995 |
| GB | 2214354 | 8/1989 | WO | WO 96/19255 | 6/1996 |
| GB | 2257269 | 1/1993 | WO | WO 97/10022 | 3/1997 |
| JP | 58-8522 | 1/1983 | WO | WO 97/25914 | 7/1997 |
| JP | 60091858 | 5/1985 | WO | WO 97/43949 | 11/1997 |
| JP | 61022752 | 1/1986 | WO | WO 97/44083 | 11/1997 |
| JP | 62023361 | 1/1987 | WO | WO 97/44086 | 11/1997 |
| JP | 62089470 | 4/1987 | WO | WO 98/10694 | 3/1998 |
| JP | 62299277 | 12/1987 | WO | WO 99/04847 | 2/1999 |
| JP | 6393516 | 4/1988 | WO | WO 99/11313 | 3/1999 |
| JP | 63-181774 | 7/1988 | WO | WO 00/27303 | 5/2000 |
| JP | 63217966 | 9/1988 | WO | WO 00/30710 | 6/2000 |
| JP | 1089956 | 4/1989 | WO | WO 00/48645 | 8/2000 |
| JP | 1135363 | 5/1989 | WO | WO 00/57943 | 10/2000 |
| JP | 1158936 | 6/1989 | WO | WO 00/66199 | 11/2000 |
| JP | 2107268 | 4/1990 | WO | WO 00/67845 | 11/2000 |
| JP | 3081831 | 4/1991 | WO | WO 00/72907 | 12/2000 |
| JP | 03-122850 | 12/1991 | WO | WO 01/28620 | 4/2001 |
| JP | 4061840 | 2/1992 | WO | WO 01/36034 | 5/2001 |
| JP | 4099963 | 3/1992 | WO | 0145912 | 6/2001 |
| JP | 4213069 | 8/1992 | WO | WO 01/45773 | 6/2001 |
| JP | 4213070 | 8/1992 | WO | WO 01/93920 | 12/2001 |
| JP | 4236965 | 8/1992 | WO | WO 02/13682 | 2/2002 |
| JP | 5149969 | 6/1993 | WO | WO 02/062540 | 8/2002 |
| JP | 5-506806 | 10/1993 | WO | WO 03/004086 | 1/2003 |
| JP | 5-309519 | 11/1993 | WO | WO 03/008148 | 1/2003 |
| JP | 5-507857 | 11/1993 | WO | WO 2004/012804 | 2/2004 |
| JP | 6-501179 | 2/1994 | WO | 2004047899 | 6/2004 |
| JP | 631749 | 4/1994 | | | |

* cited by examiner

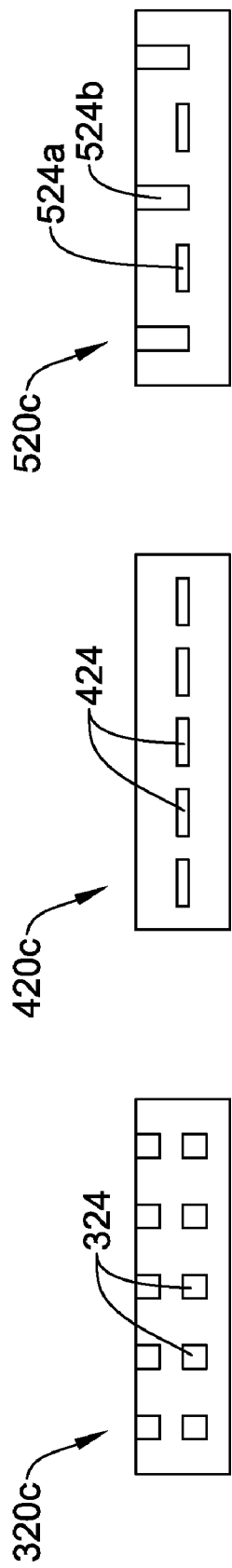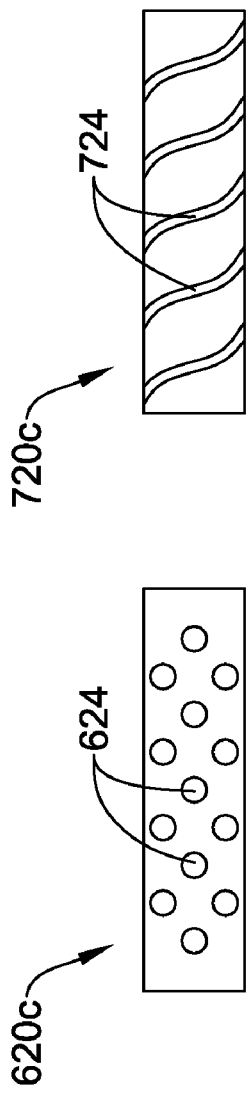

TUBULAR MEMBER HAVING TAPERED TRANSITION FOR USE IN A MEDICAL DEVICE

CROSS-REFERENCE TO RELATED APPLICATIONS

This application is a continuation-in-part of U.S. patent application Ser. No. 10/604,504, filed Jul. 25, 2003, now U.S. Pat. Pub. No. US 2004/0181174, which claims priority to U.S. Provisional App. No. 60/399,046, filed Jul. 25, 2002, the disclosures of which are incorporated herein by reference.

FIELD OF THE INVENTION

The present invention pertains to intracorporal medical devices, for example, intravascular guidewires, catheters, and the like as well as improved methods for manufacturing and using such medical devices. More particularly, the invention relates to an elongate tubular member including a tapered transition portion, and medical devices including such a tubular member.

BACKGROUND

A wide variety of intracorporeal medical devices have been developed for medical use, for example, intravascular use. Some of these devices include guidewires, catheters, and the like. Of the known medical devices, each has certain advantages and disadvantages. There is an ongoing need to provide alternative medical devices as well as alternative methods for manufacturing and using medical devices.

BRIEF SUMMARY

The invention provides design, material, and manufacturing method alternatives for intracorporal medical devices. An example embodiment includes a tubular member including a tapered transition region disposed between two sections having different physical characteristics, such as flexibility characteristics. Some example embodiments include a medical device including such a tubular member. Some of these and other features and characteristics of some example inventive devices and methods are described in more detail below.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 11 is a side view of an example arrangement of slots for a tubular member;

FIG. 12 is a side view of another example arrangement of slots for a tubular member;

FIG. 13 is a side view of another example arrangement of slots for a tubular member;

FIG. 14 is a side view of another example arrangement of slots for a tubular member; and FIG. 15 is a perspective view of another example arrangement of slots for a tubular member.

Figure 1:
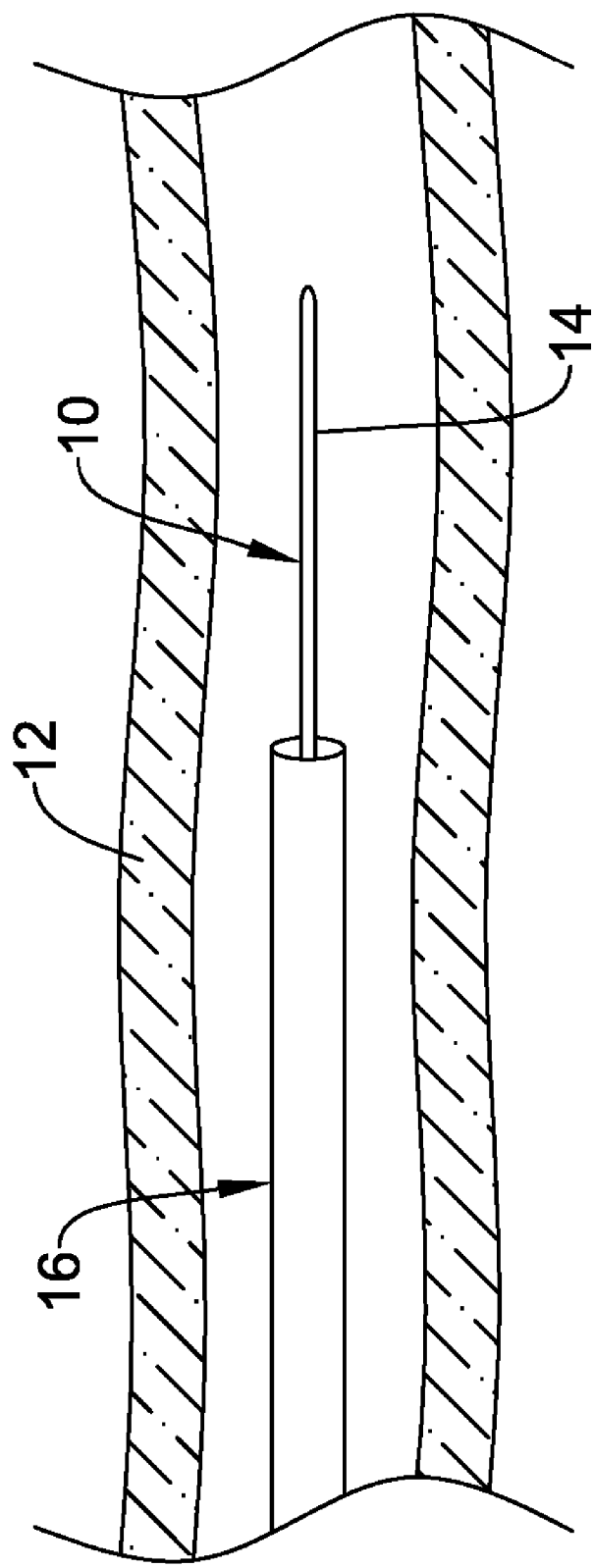
FIG. 1 is a plan view of an example medical device disposed in a blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example medical device 10, for example a guidewire, disposed in a blood vessel 12. Guidewire 10 may include a distal section 14 that may be, as is well known in the art, generally configured for probing within the anatomy of a patient. Guidewire 10 may be used for intravascular procedures according to common practice and procedure. For example, guidewire 10 may be used in conjunction with another medical device 16, which may take the form of a catheter, to treat and/or diagnose a medical condition. Of course, numerous other uses are known amongst clinicians for guidewires and other similarly configured medical devices.

Because medical devices may need to navigate the tortuous anatomy, there are a number of design considerations that are often contemplated when manufacturing medical devices like guidewire 10 and/or catheter 16. For example, it may be desirable to design medical devices that have a generally soft or rounded distal tip so as to reduce the trauma that could otherwise be associated with interactions between the medical device and a blood vessel. In addition, it is often desirable for at least the distal region of the medical device to be highly flexible so that it can bend while navigating the vasculature. Moreover, because medical devices are often inserted into the body at a location that is a distance from the target site, medical devices are typically designed with sufficient column strength so that a clinician can push the device at a proximal location and have it advance into and through the vasculature. This design consideration, often termed "pushability", may be embodied by a generally stiff proximal section of the medical device. In addition, because it may be desirable for a clinician to apply torque at one end of the device and have the torque translate to the other end, for example when advancing and/or navigating the device through the anatomy, medical devices are often designed to possess a certain level of "torquability" or the ability to transmit torque from the proximal end to the distal end.

The medical devices disclosed herein may take into account these and other design considerations. Accordingly, in some embodiments, to the extent applicable, the example medical devices disclosed herein may generally include structural features that may contribute to some of these characteristics. While the discussion found below is generally attributed to guidewire 10, it should be noted that the invention is not intended to be limited to guidewires as numerous other medical devices are contemplated. For example, the device may comprise a catheter (e.g., therapeutic, diagnostic, or guide catheter) like catheter 16, or catheters 610 and 710 discussed below, or an endoscopic device, a laproscopic device, a stent, an embolic or distal protection device, or any other suitable device.

Figure 2:
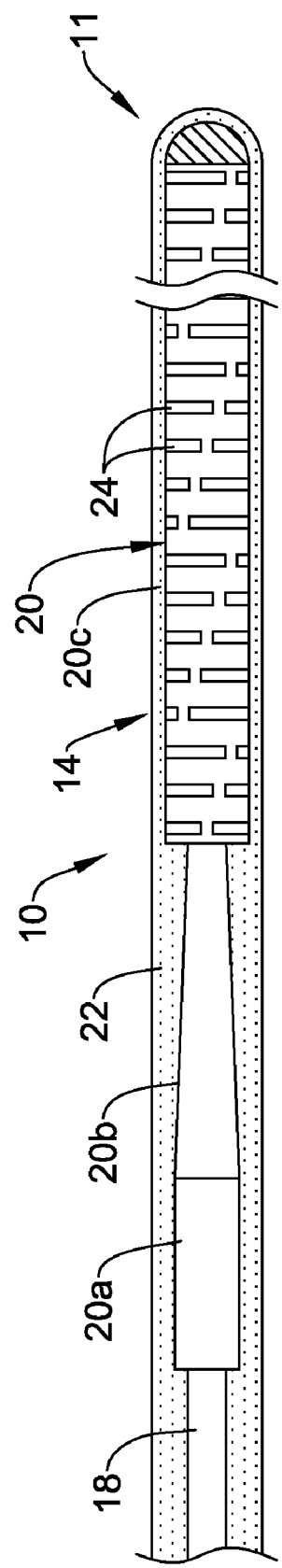
FIG. 2 is a partially cut-away side view of an example medical device.

Turning now to FIG. 2, distal section 14 of guidewire 10 is illustrated. Here it can be seen that guidewire 10 may include an inner member, such as a core wire 18, and a tubular member 20 disposed over at least a portion of core wire 18. In some embodiments, core wire 18 may extend to the distal end of tubular member 20. In other embodiments, tubular member 20 may extend distally beyond the distal end of core wire 18.

A sheath or covering 22 may be disposed over portions or all of core wire 18 and/or tubular member 20 that may define a generally smooth outer surface for guidewire 10. In other embodiments, however, such a sheath or covering 22 may be absent from a portion or all of guidewire 10, such that tubular member 20 and/or core wire 18 may form the outer surface. In FIG. 2, the sheath or covering 22 is partially cut away to show a side view of core wire 18 and tubular member 20. A rounded or generally atraumatic distal tip 11 can be formed at the distal end of guidewire 10. Core wire 18 may extend to and/or into distal tip 11, or may end proximally thereof. The tubular member 20 can be attached to the core wire 18 in any suitable manner. For example, the tubular member 20 and core wire 18 can be attached at the proximal end of tubular member 20, the distal end of tubular member 20, both, and/or at any suitable position there between, using any of a wide variety or suitable attachment techniques, such as welding, soldering, brazing, adhesives, mechanical fitting and/or crimping, or the like. In the embodiment shown, the core wire 18 extends proximally from the proximal end of the tubular member 20, but it should be understood that in other embodiments, the tubular member 20 may extend further proximally, for example, to the proximal end of the device. Some additional description regarding the attachment of core members and tubular members, and various structures and constructions of medical devices including slotted tubular members can be found in U.S. patent application Ser. No. 10/604,504 (Pub. No. 2004/0181174-A2), the entire contents of which are herein incorporated by reference.

In at least some embodiments, tubular member 20 includes a first section 20a, a tapered section 20b, and a slotted section 20c. In general, the longitudinal arrangement of sections 20a/20b/20c can be as shown in FIG. 2. For example, the tapered section 20b may be generally disposed between the first section 20a and the slotted section 20c. In at least some embodiments, tubular member 20 may be a single, continuous and/or uninterrupted tube having sections 20a/20b/20c. In other embodiments, portions of tubular member 20 may include discrete tubular sections that are attached to one another. For example, first section 20a and tapered section 20b may be an uninterrupted "first" tubular member that is attached to a "second" tubular member that defines slotted section 20c. Collectively, the attached "first" and "second" tubular members define tubular member 20. Alternatively, tapered section 20b and slotted section 20c may be a single, continuous "first" tubular member that is attached to a "second" tubular member defining first section 20a to define tubular member 20. In still other alternative embodiments, all three sections 20a/20b/20c may be discrete tubular sections that are joined together to define tubular member 20. In some embodiments, additional sections and/or components may be added to the tubular member 20 as desired.

As the name implies, slotted section 20c can include a plurality of slots 24 formed therein. In some embodiments, only section 20c includes slots 24 and sections 20a/20b are free of slots 24. In other embodiments, section 20a, section 20b, or both may include one or more slots 24.

Slots 24 may be micromachined or otherwise created in tubular member 20, and may be configured to make tubular member 20 more flexible in bending. The slots 24 may enhance the bending flexibility of the tubular member 20 without significantly reducing and/or hampering the torque transmission characteristics of the tubular member 20. Any of the above mentioned slots 24 can be formed in essentially any known way. For example, slots 24 can be formed by methods such as micro-machining, saw cutting (e.g., diamond grit embedded semiconductor dicing blade), laser cutting, grinding, milling, casting, molding, chemically etching or treating, electron discharge machining, or the like, or other known methods, and the like. Some example embodiments of appropriate micromachining methods and other cutting methods, and structures for tubular members including slots and medical devices including tubular members are disclosed in U.S. Pat. Publication Nos. US 2003/0069522; and US 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 10 may include forming slots 24 in tubular member 20 using any of these or other manufacturing steps.

Various embodiments of arrangements and configurations of slots 24 are contemplated. Slots 24 may be generally arranged to be perpendicular to the longitudinal axis of tubular member 20. This arrangement can, alternatively, be described as having slots 24 lying within a plane that is normal to the longitudinal axis of tubular member 20. In other embodiments, slots 24 may be formed at an angle relative to a plane that is normal to the longitudinal axis. In some embodiments, slots 24 may be formed part way through tubular member 20, while in other embodiments, slots 24 may extend all the way through tubular member 20. Any one or more of the individual slots 24 may extend only partially around the longitudinal axis of tubular member 20. In yet other embodiments, slots 24 may extend in a helical arrangement about the longitudinal axis of tubular member 20. Slots 24 may be formed in groups of two, three, or more slots 24, which may be located at substantially the same location along the axis of tubular member 20, and may be substantially perpendicular to the longitudinal axis. In other embodiments, only one slot 24, rather than a group of slots, may be disposed at one or more locations along the axis of tubular member 20. These embodiments may or may not include groups of slots 24 at other locations along the axis of tubular member 20.

The tubular member 20 may be included in the structure of the medical device to provide certain characteristics, for example, to enhance torque transmission, while still allowing for desired flexibility characteristics. When a tubular member, such as a slotted tubular member, is used in a medical device, it may be desirable to create a smooth transition in axial and torsional stiffness from a stiffer section of tubular member (e.g., an "unslotted" first section 20a of tubular member 20) to a more flexible section of tubular member (e.g., slotted section 20c of tubular member 20). This may help to reduce, for example, kinking that might otherwise occur at abrupt changes in flexibility. Some ways to establish this transition is to distally increase the frequency of slots 24, distally decrease the spacing of slots 24, distally increase the size of slots 24, or combinations thereof, or the like.

The embodiment shown in FIG. 2 represents an example of another and/or additional way to make this transition. Here, the transition or tapered section 20b is disposed between the first section 20a and slotted section 20c. For example, the first section 20a, which may be a proximal section, may generally have a first flexibility characteristic, such as being generally stiff or less flexible, for example, to enhance pushability. For example, in at least some embodiments, the first section 20a may be "unslotted" or substantially free of any slots formed therein, thereby providing it with a desired level of stiffness. The slotted section 20c, which may be a distal section, generally has a second flexibility characteristic that is more flexible than first section 20a, for example, to enhance bending and/or steering characteristics, or the like. The tapered section 20b may be an intermediate section disposed between the sections 20a and 20c, and may be tapered to provide a transition in flexibility characteristics between the sections 20a and 20c. For example, the outer diameter and/or perimeter of the transition section 20b may taper from a larger dimension adjacent the first section 20a to a smaller dimension adjacent the slotted section 20c. This tapering in the size and/or amount of material in the transition section 20b can provide for a desired transition in flexibility characteristics between the first and slotted sections 20a/20c, and reduce the occurrence of an abrupt change in flexibility characteristics.

The tapering of the tapered section 20c can be provided as desired, to achieve the desired transition. For example, the tapering can be provided in a linear, stepwise, curvilinear, or other fashion, as desired. In some embodiments, the flexibility characteristics of the tapered section 20b can be generally characterized as being intermediate to those of the first section 20a and the slotted section 20c, but generally, there is some transition of flexibility characteristics along the length of the tapered section 20b, moving from less flexibility adjacent the first section 20a to more flexibility adjacent the slotted section 20c. The transition can evolve from a flexibility that is at or near the flexibility of first section 20a, to a flexibility that is less than first section 20a, to a flexibility that approaches the flexibility of slotted section 20c. This arrangement of first section 20a, tapered section 20b, and slotted section 20c, thus, can create a desirable generally smooth transition in flexibility along the longitudinal axis of tubular member 20 between the sections 20a and 20c. Moreover, because first section 20a, tapered section 20b, and slotted section 20c, collectively, are generally made from a tubular material, tubular member 20 can provide the medical device 10 with an increased level of axial and/or torsional stiffness, while also providing the desired flexibility characteristics along its length.

Forming tapered section 20b, and/or other sections 20a and 20c of the tubular member 20, may include any one of a number of different techniques. For example, the sections of the tubular member 20, including the tapered section 20b, may be formed by centerless grinding methods, casting or forming methods, stamping methods, and the like. The centerless grinding technique may utilize an indexing system employing sensors (e.g., optical/reflective, magnetic) to avoid excessive grinding. In addition, the centerless grinding technique may utilize a CBN or diamond abrasive grinding wheel that is well shaped and dressed to avoid grabbing tubular member 20 during the grinding process. In some embodiments, tubular member 20 is centerless ground using a Royal Master HI-AC centerless grinder.

The materials that can be used for the various components of guidewire 10 may include those commonly associated with medical devices. For example, core wire 18 and/or tubular member 20 may be made from a metal, metal alloy, a metal-polymer composite, and the like, or any other suitable material. Some examples of suitable metals and metal alloys include stainless steel, such as 304V, 304L, and 316LV stainless steel such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, other HASTELLOY® alloys, and the like), nickel-chromium-iron alloy, nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), other nickel-chromium alloys, other nickel-molybdenum alloys, other nickel-cobalt alloys, other nickel-iron alloys, other nickel-copper alloys, other nickel-tungsten alloys; tungsten or tungsten alloys; cobalt alloys, such as cobalt-chromium alloys; cobalt-chromium-molybdenum alloys (e.g., UNS: R30003 such as ELGILOY®, PHYNOX®, and the like); tungsten or tungsten alloys; platinum enriched stainless steel; 17-4PH®; 17-7PH®; 18Cr-2Ni-12Mn; 20Cb-3®; 21Cr-6Ni-9Mn; 22Cr-13Ni-5Mn302; 35N LT®; other stainless steels (e.g., 302, 304LV, 316LVM, 321, 347, etc.); 446A286; 455®; Alloy 31; Alloy 41; Alloy 600; Alloy 625; Alloy 718; Alloy 901; Alloy 902; Alloy B; Alloy X-750CCM®; Chromel; CONICHROME®; CP Ti Gr1; CP Ti Gr1HP; CP Ti Gr2; CP Ti Gr3; CP Ti Gr4 UnAlloyed (CP); Ti-Osteum®; Ti-3Al-2.5V; CUSTOM 455®; CUSTOM 465®; DBS®; DFT® (Composite); HASTELLOY Alloy C-4; HASTELLOY Alloy S; HASTELLOY Alloy X; HAYNES® 188; HAYNES 214™; HAYNES 230™; HAYNES 242™; HAYNES Alloy C-263; Hiperco 50B; INCONEL® Alloy 617; INCONEL Alloy 601; L605; Ni200; NIMONIC® 90; Platinum; Platinum-10 Iridium; Platinum-10 Nickel; Platinum-20 Iridium; Platinum-5 Iridium; Silver; Tantalum; Ti-13Zr-13Nb; Ti-3Al-8V-6Cr-4Zr-4Mo; Ti-6Al- 4V ELI; Ti-6Al-4Zr-2Sn-2Mo; Ti-6Al-7Nb; Ti-8Al-1Mo-1V; ULTIMET®; WASPALOY®; combinations thereof; or the like; or any other suitable material.

As alluded to above, within the family of commercially available nickel-titanium or nitinol alloys, is a category designated "linear elastic" which, although it may be similar in chemistry to conventional shape memory and superelastic varieties, exhibits distinct and useful mechanical properties. By the applications of cold work, directional stress, and heat treatment, the material is fabricated in such a way that it does not display a substantial "superelastic plateau" or "flag region" in its stress/strain curve. Instead, as recoverable strain increases, the stress continues to increase in a generally linear relationship (as compared to that of super-elastic material, which has a super-elastic plateau) until plastic deformation begins. In some embodiments, the linear elastic nickel-titanium alloy is an alloy that does not show any substantial martensite/austenite phase changes that are detectable by DSC and DMTA analysis over a large temperature range.

For example, in some embodiments, there are no substantial martensite/austenite phase changes detectable by DSC and DMTA analysis in the range of about −60° C. to about 120° C. The mechanical bending properties of such material are therefore generally inert to the effect of temperature over this very broad range of temperature. In some particular embodiments, the mechanical properties of the alloy at ambient or room temperature are substantially the same as the mechanical properties at body temperature. In some embodiments, the use of the linear elastic nickel-titanium alloy allows the guidewire to exhibit superior "pushability" around tortuous anatomy. Accordingly, components of guidewire 10 such as core wire 18 and/or tubular member 20 may include linear elastic nickel-titanium alloy.

In some embodiments, the linear elastic nickel-titanium alloy is in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. In some other embodiments, a superelastic alloy, for example a superelastic nitinol can be used to achieve desired properties.

In at least some embodiments, portions or all of core wire 18 and/or tubular member 20, or other components that are part of or used in the device, may be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of guidewire 10 to achieve the same result.

In some embodiments, a degree of MRI compatibility is imparted into device 10. For example, to enhance compatibility with Magnetic Resonance Imaging (MRI) machines, it may be desirable to make core wire 18 and/or tubular member 20, or other portions of the medical device 10, in a manner that would impart a degree of MRI compatibility. For example, core wire 18 and/or tubular member 20, or portions thereof, may be made of a material that does not substantially distort the image and create substantial artifacts (artifacts are gaps in the image). Certain ferromagnetic materials, for example, may not be suitable because they may create artifacts in an MRI image. Core wire 18 and/or tubular member 20, or portions thereof, may also be made from a material that the MRI machine can image. Some materials that exhibit these characteristics include, for example, tungsten, Elgiloy, MP35N, nitinol, and the like, and others.

Referring now to core wire 18, the entire core wire 18 can be made of the same material along its length, or in some embodiments, can include portions or sections made of different materials. In some embodiments, the material used to construct core wire 18 is chosen to impart varying flexibility and stiffness characteristics to different portions of core wire 18. For example, the proximal region and the distal region of core wire 18 may be formed of different materials, for example materials having different moduli of elasticity, resulting in a difference in flexibility. In some embodiments, the material used to construct the proximal region can be relatively stiff for pushability and torqueability, and the material used to construct the distal region can be relatively flexible by comparison for better lateral trackability and steerability. For example, the proximal region can be formed of straightened 304v stainless steel wire or ribbon and the distal region can be formed of a straightened super elastic or linear elastic alloy, for example a nickel-titanium alloy wire or ribbon.

In embodiments where different portions of core wire 18 are made of different materials, the different portions can be connected using any suitable connecting techniques. For example, the different portions of core wire 18 can be connected using welding (including laser welding), soldering, brazing, adhesive, or the like, or combinations thereof. Additionally, some embodiments can include one or more mechanical connectors or connector assemblies to connect the different portions of core wire 18 that are made of different materials. The connector may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Some other examples of suitable techniques and structures that can be used to interconnect different shaft sections are disclosed in U.S. patent application Ser. No. 09/972,276 filed on Oct. 5, 2001, 10/086,992 filed on Feb. 28, 2002, and 10/375,766 filed on Feb. 26, 2003, which are incorporated herein by reference.

Core wire 18 can have a solid cross-section, but in some embodiments, can have a hollow cross-section. In yet other embodiments, core wire 18 can include a combination of areas having solid cross-sections and hollow cross sections. Moreover, core wire 18, or portions thereof, can be made of rounded wire, flattened ribbon, or other such structures having various cross-sectional geometries. The cross-sectional geometries along the length of core wire 18 can also be constant or can vary. For example, FIG. 2 depicts core wire 18 as having a round cross-sectional shape. It can be appreciated that other cross-sectional shapes or combinations of shapes may be utilized without departing from the spirit of the invention. For example, the cross-sectional shape of core wire 18 may be oval, rectangular, square, polygonal, and the like, or any suitable shape. Additionally, the core wire 18 may include one or more tapered portions, for example, to provide for desired flexibility characteristics. Such tapers can be made or exist in a linear, stepwise, curvilinear, or other suitable fashion to achieve the desired results.

Sheath 22 may be made from a polymer or any other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In some embodiments sheath 22 can be blended with a liquid crystal polymer (LCP). For example, the mixture can contain up to about 6% LCP. This has been found to enhance torqueability. By employing selection of materials and processing techniques, thermoplastic, solvent soluble, and thermosetting variants of these and other materials can be employed to achieve the desired results.

In some embodiments, a coating, for example a lubricious, a hydrophilic, a protective, or other type of coating may be applied over portions or all of sheath 22, or in embodiments without a sheath 22, over portion of core wire 18 and/or tubular member, or other portions of device 10. Alternatively, sheath 22 may comprise a lubricious, hydrophilic, protective, or other type of coating. Hydrophobic coatings such as fluoropolymers may provide a dry lubricity which improves guidewire handling and device exchanges. Lubricious coatings may improve steerability and improve lesion crossing capability. Some examples of suitable coating materials may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Some coating polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The sheath 22 may be formed, for example, by coating, extrusion, co-extrusion, interrupted layer co-extrusion (ILC), heat bonding, shrink bonding, or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention. Any coating can also be formed and/or deposited using any suitable technique, such as spray coating, dip coating, or the like, or using any of the application techniques discussed above regarding the sheath 22.

Figure 3:
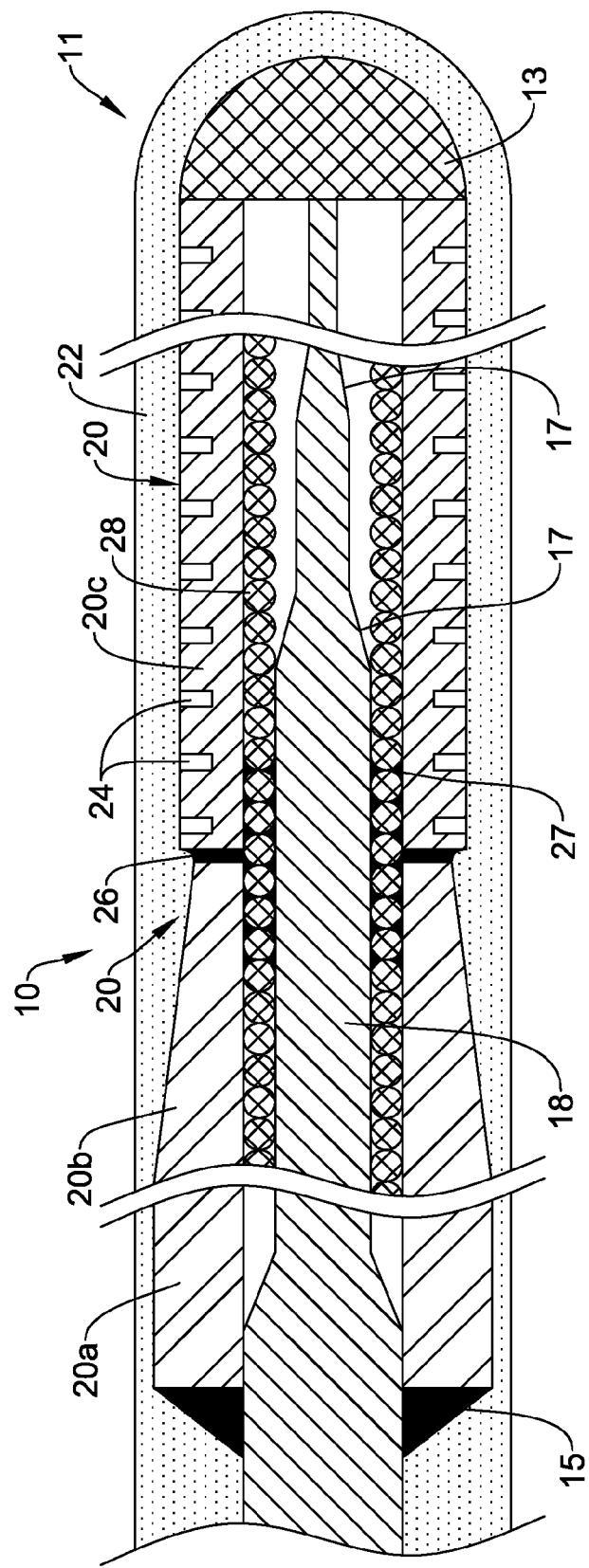
FIG. 3 is a cross-sectional side view of a portion of the device shown in FIG. 2.

FIG. 3 illustrates a portion of guidewire 10 in cross-section. In this embodiment, it can be seen that sections of the tubular member 20 may be discrete tubular members or components that are attached, joined or bonded together in a suitable manner. For example, in FIG. 3, the tapered section 20b and slotted section 20c of tubular member 20 can be discrete tubular members or components that are attached using any suitable joining or bonding technique, such as adhesive bonding, welding, soldering, brazing, or the like, or any other suitable method. The joining technique may create a bonding or attachment zone or region 26 wherein sections 20b/20c are attached. Depending on the particular attachment technique utilized, a material such as a weld, adhesive, braze, solder, or the like, for example, may be disposed at attachment zone 26. Additionally, attachment zone 26 may also be disposed between tubular member 20 and core wire 18, thereby attaching the tubular member 20, or sections thereof, to the core wire 18 at this location, if so desired. Other sections and/or portions of the tubular member, such as first section 20a, may be attached in a similar manner. Alternatively, the first section 20a and tapered section 20b may be an uninterrupted "first" tubular member that is attached to a "second" tubular member that defines slotted section 20c.

It can also be seen in FIG. 3 that an intermediate member 28 may be disposed between the outer surface or diameter of the core wire 18 and the inner surface or diameter of the tubular member 20. In the embodiment shown in FIG. 3, the intermediate member is a coil 28, but in other embodiments, other structures, such as a tubular sleeve or jacket may be used. In some embodiments, the intermediate member 28 may aid in securing different sections of the tubular member 20 to one another, for example, by providing an overlapping structure to the joint. For example, the intermediate member 28 may extend longitudinally within a portion of the tubular member 20 such that it overlaps with and is secured to different sections of the tubular member, such as sections 20b and 20c. As such, the intermediate member 28 overlaps with the bonding zone 26, and can aid in connecting the sections 20b and 20c together. The bonding technique or techniques used to connect the sections 20b and 20c together may also act to connect each of the sections 20b and 20c to the intermediate member 28, or separate bonding of the intermediate member 28 to the tubular member 20 may occur. The intermediate member 28 may also function to center the core wire 18 within the tubular member 20, and may be adapted to provide desired characteristics, such stiffness, flexibility, radiopacity, or the like.

Additionally, in some embodiments, the intermediate member 28 may function to secure the tubular member 20 with core wire 18. For example, in addition to being attached to the tubular member 20 and/or sections thereof, the intermediate member 28 may also be attached to the core wire 18, for example at bonding zone 27. The attachment of the intermediate member 28 to the core wire 18 can be made using a separate attachment technique, or can be made at the same time and/or using the same technique used to attach the tubular member 20 to the intermediate member 28. For example, in embodiments where a bonding material, such as an adhesive, solder, weld, or brazing material is used to make the attachment at the attachment zone 26, the material can be allowed to flow or wick between winding of coil 28 or otherwise flow from tubular member 20 onto coil 28 and into contact with core wire 18, thereby attaching the coil 28 to the core wire 18, and the coil to the tubular member 20. In such embodiments, the bonding zones 26 and 27 can essentially be formed using the same attachment technique or bonding material. Again, this type of arrangement can improve the attachment between tubular member 20 and core wire 18. A number of other structural components can be used for the intermediate member in place of the coil 28, such as a slotted or porous sleeve, jacket, or the like. The intermediate member, such as the coil 28, may extend distally to distal tip 11, proximally, for example to the proximal end of the tubular member 20, or beyond, or may end at any suitable location within the tubular member 20. It should be understood, however, that in some embodiments, the intermediate member 28 may not be attached to the core wire 18, or at least not attached to the core wire 18 at the longitudinal location of the bonding zone 26. In such embodiments, the core wire 18 may be at least somewhat free to move longitudinally relative to the intermediate member 28 and/or tubular member 20, for example, when the device is bent or flexed laterally. It should also be appreciated, that such an intermediate member 28 is not necessary in all embodiments, as will be discussed and illustrated further below.

FIG. 3 also shows that the tubular member 20 can be attached, for example, at its proximal and distal ends to the core wire 18. As should be understood, other locations for the attachment may be suitable. In this example, the distal end of the core wire 18 can be attached to the distal end of the tubular member 20 through a distal tip member 13, such as a solder tip or the like. Additionally, one or more proximal attachment zones 15 may attach the core wire to the tubular member 20, and the core wire 18 may extend proximally from the proximal end of the tubular member 20. Additionally, this embodiment shows the core wire 18 including one or more tapered sections 17, for example, in the distal section of the core wire, which may provide for desired flexibility characteristics, or the like. As indicated above, however, many of a broad variety of alternative constructions, assemblies, and/or arrangements may be used. Some additional description regarding the attachment of core members and tubular members, and various structures and constructions of medical devices including slotted tubular members and tip constructions can be found in U.S. patent application Ser. No. 10/604,504 (Pub. No. 2004/0181174-A2), the entire contents of which are herein incorporated by reference.

Figure 4:
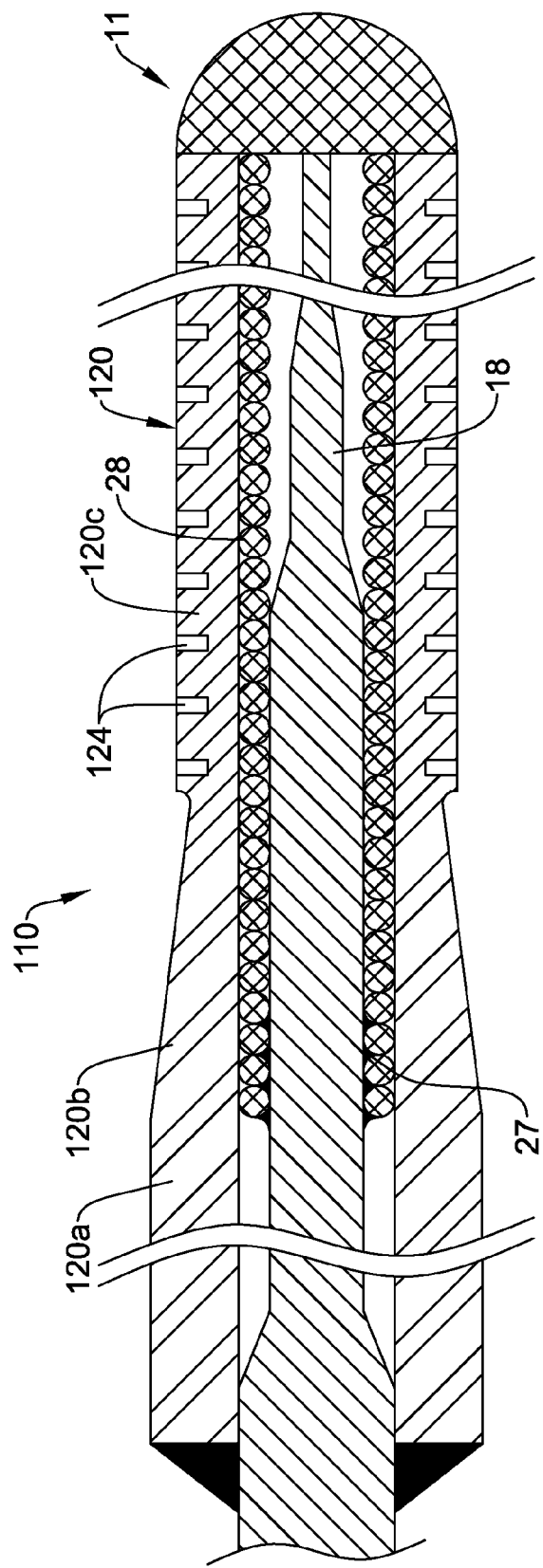
FIG. 4 is a cross-sectional side view of a portion of another example medical device.

FIG. 4 shows another example of a guidewire 110 which is similar in some respects to guidewire 10, wherein like reference numbers indicate similar structure. In the guidewire 110 of FIG. 4, however, the tubular member 120 is formed from a continuous or one-piece or singular member that defines first section 120a, tapered section 120b, and slotted section 120c. The sections 120a, 120b, and 120c can include structure and/or be arranged or disposed in a similar manner to the sections 20a, 20b, and 20c, as discussed above, but are simply all formed in a single tubular material. In other words, the tubular member 120 may be a single monolith of material that defines sections 120a, 120b, and 120c. According to this embodiment, a singular tubular starting material can be, for example, cut, ground, or otherwise worked, made, or shaped so as to define the sections 120a, 120b, and 120c.

FIG. 4 also illustrates that an outer sheath can be omitted from any of the embodiments of the medical devices disclosed herein. However, it still may be desirable to create a smooth outer surface for guidewire 110 (or any of the other devices). For example, the exterior surface of the guidewire 110 (and/or any other guidewire disclosed herein) may include a coating or covering, be sandblasted, be beadblasted, be sodium bicarbonate-blasted, be electropolished, plated, or the like, or otherwise treated or worked to provide the desired surface.

FIG. 4 also shows an intermediate member 28, in this case a coil 28, disposed between the tubular member 20 and the core wire 18, and attached to the core wire 18. In this embodiment, the intermediate member 28 extends distally to the distal tip 11. However, as indicated above, in some other embodiments, the intermediate member 28 may be absent, or may be present, but attached or bonded to the tubular member 20, or to both the tubular member 18 and the core wire 18. In addition, the position of the bonding or attachment points to either or both the core wire 18 and/or tubular member may be at alternative locations along the length of the coil 28.

Figure 5:
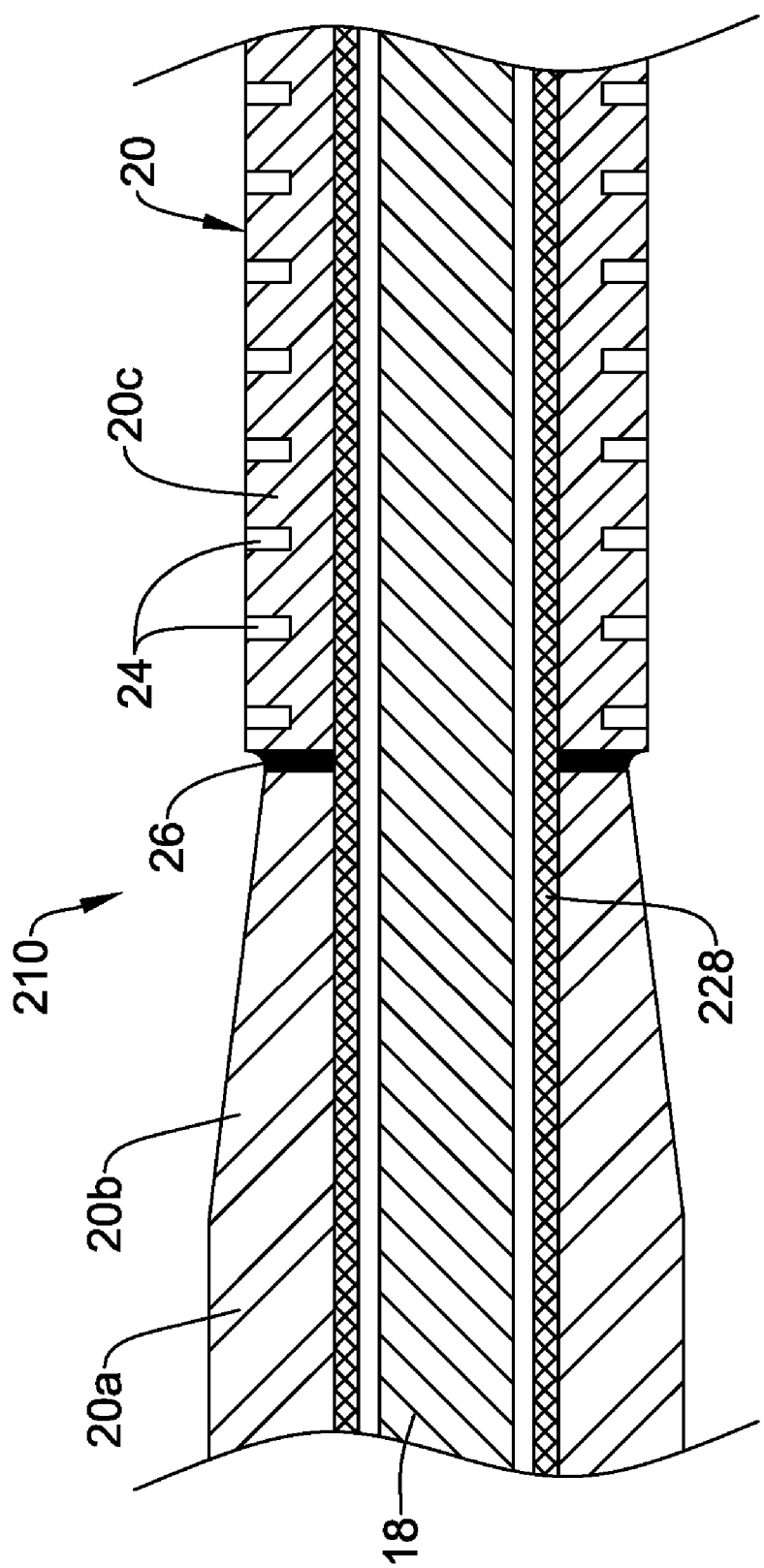
FIG. 5 is a cross-sectional side view of a portion of another example medical device.

FIG. 5 illustrates another embodiment of a guidewire 210, similar in some respects to guidewires discussed above, wherein like reference numbers indicate similar structure. In this embodiment, however, an intermediate member 228 is a sleeve or jacket of material, rather than a coil. The sleeve or jacket 228 may be made from any material suitable for attaching to the tubular member 20. Some examples of suitable material may include a metal, metal alloy, a metal-polymer composite, and the like, or any other suitable material, for example, those materials disclosed herein. As can be appreciated, the intermediate member 228 may aid in securing different sections of the tubular member 20 to one another, for example, by providing an overlapping structure to the joint, for example as discussed in the embodiment of FIG. 3 above. For example, the intermediate member 228 may extend longitudinally within a portion of the tubular member 20 such that it overlaps with and is secured to different sections of the tubular member, such as sections 20b and 20c. As such, the intermediate member 228 overlaps with the bonding zone 26, and can aid in connecting the sections 20b and 20c together. The bonding technique or techniques used to connect the sections 20b and 20c together may also act to connect each of the sections 20b and 20c to the intermediate member 128, or separate bonding of the intermediate member 228 to the tubular member 20 may occur. The bonding technique or techniques can include any suitable technique given the materials used, for example, the bonding techniques disclosed above. As can be appreciated, in this embodiment, the intermediate member is not attached to the core wire 18 at the bonding zone 26, possibly allowing the core wire 18 to have some degree of lateral movement within the tubular member 20 at this location. The intermediate member 228 may also function to center the core wire 18 within the tubular member 20, and may be adapted to provide desired characteristics, such as stiffness, flexibility, radiopacity, or the like, to this portion of the device. The intermediate member 228 may extend distally to the distal tip, proximally, for example to the proximal end of the tubular member 20, or beyond, or may end at any suitable location within the tubular member 20.

Figure 6:
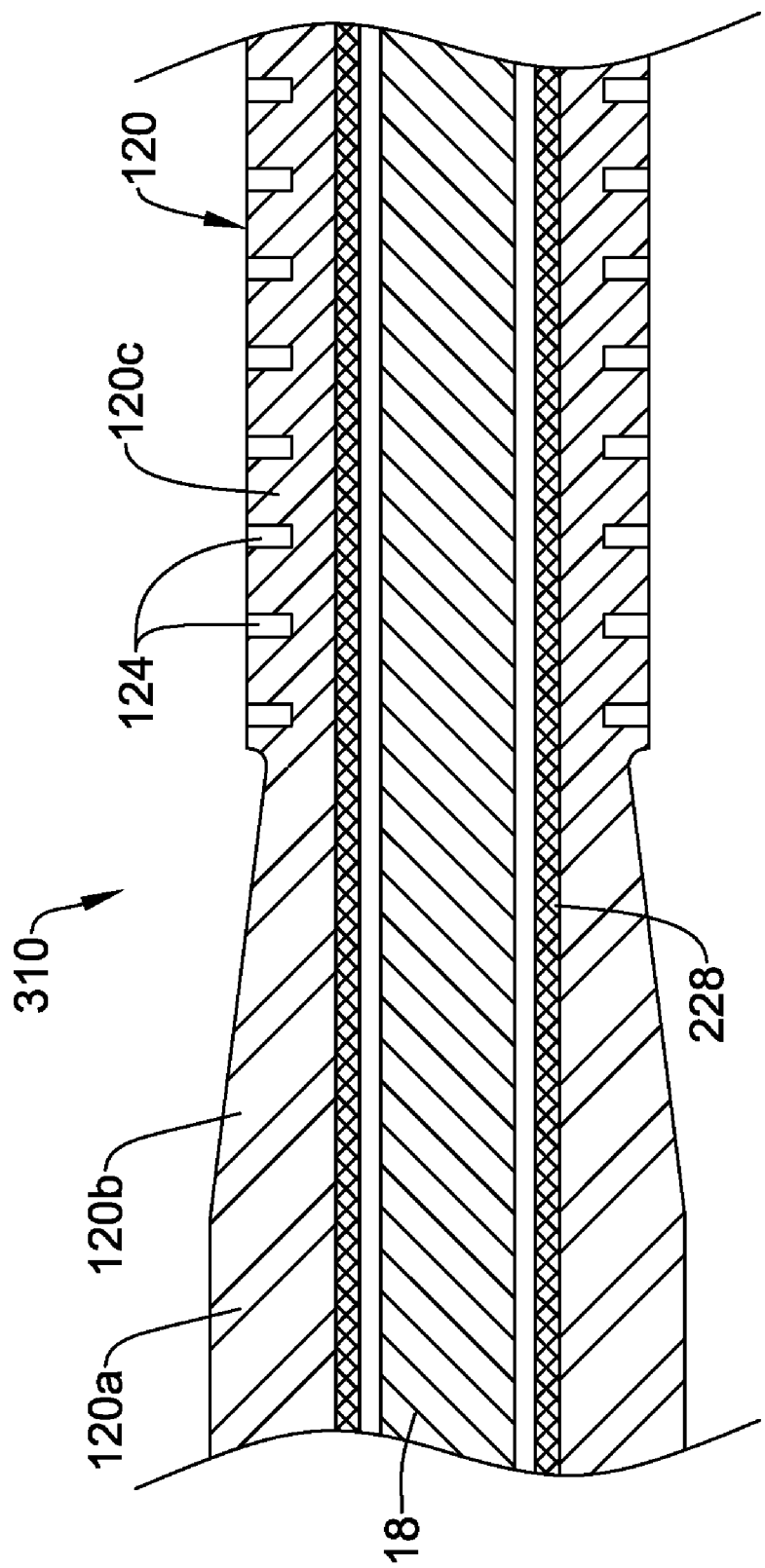
FIG. 6 is a cross-sectional side view of a portion of another example medical device.

FIG. 6 illustrates another embodiment of a guidewire 310, similar in some respects to guidewires discussed above, wherein like reference numbers indicate similar structure. In this embodiment, the intermediate member 228 is again a sleeve or jacket similar to that in guidewire 210 in FIG. 5, but the tubular member 120 is formed from a continuous or one-piece member that defines first section 120a, tapered section 120b, and slotted section 120c, similar to that shown in FIG. 4.

Figure 7:
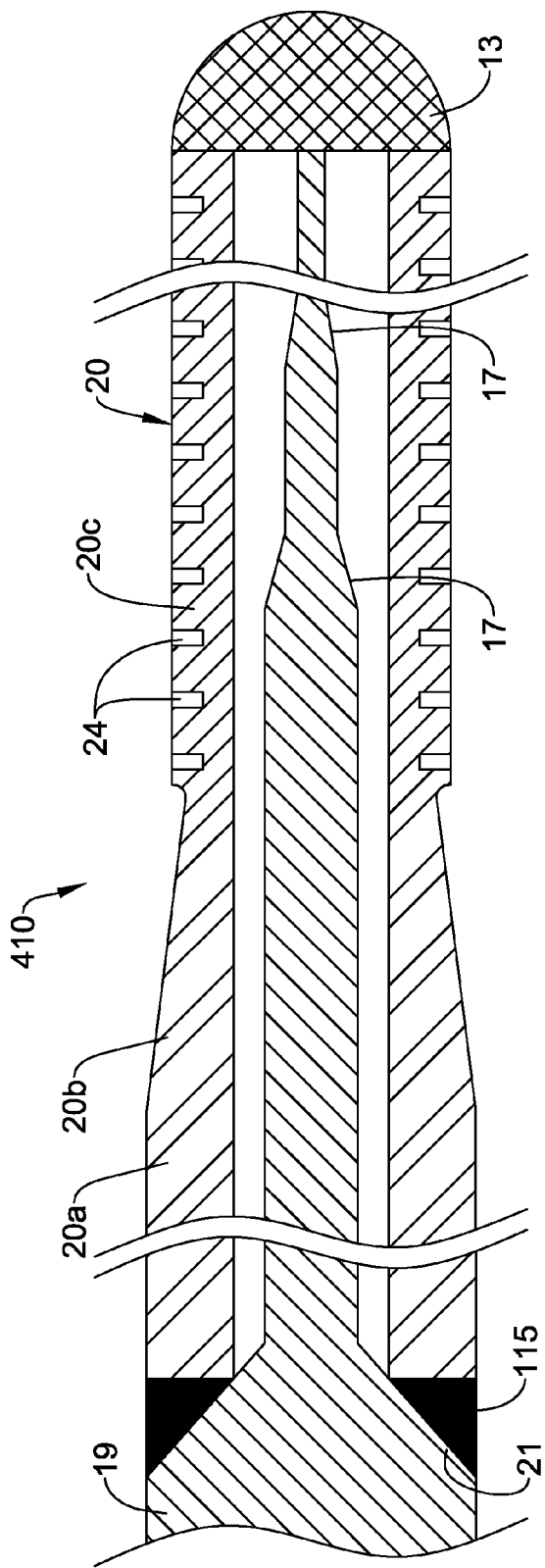
FIG. 7 is a cross-sectional side view of a portion of another example medical device.

FIG. 7 illustrates another example guidewire 410 that is similar in some respects to other devices disclosed herein, wherein like reference numbers indicate similar structure. In this embodiment, the tubular member 120 is again formed from a continuous or one-piece member that defines first section 120a, tapered section 120b, and slotted section 120c, similar to the embodiments of FIGS. 4 and 6. However, in this embodiment, there is no intermediate member disposed between the core wire 18 and the tubular member 120. Again, the tubular member 120 can be attached to the core wire 18 at any suitable location, for example, at the proximal and distal ends of the tubular member 120, and/or at other locations. As shown in this embodiment, the core wire 18 may include a proximal section 19 that has an outer diameter that is close to or the same as the outer diameter of the first section 120a of the tubular member 120, and the tubular member 120 can be attached to the core wire such that a smooth transition in the outer diameter of the device is created at the attachment zone 115. For example, the core wire 18 may include a more proximal taper 21, and the proximal end of the tubular member 120 can be attached to the core wire 18 at or near the taper 21. The attachment or bonding material within the attachment zone 115 may create a smooth transition in outer diameter between the tubular member 120 and the proximal portion 19 of the core wire 18. And again, this embodiment shows that the core wire 18 can include one or more distal tapered sections 17, which may provide for desired flexibility characteristics, or the like.

Figure 8:
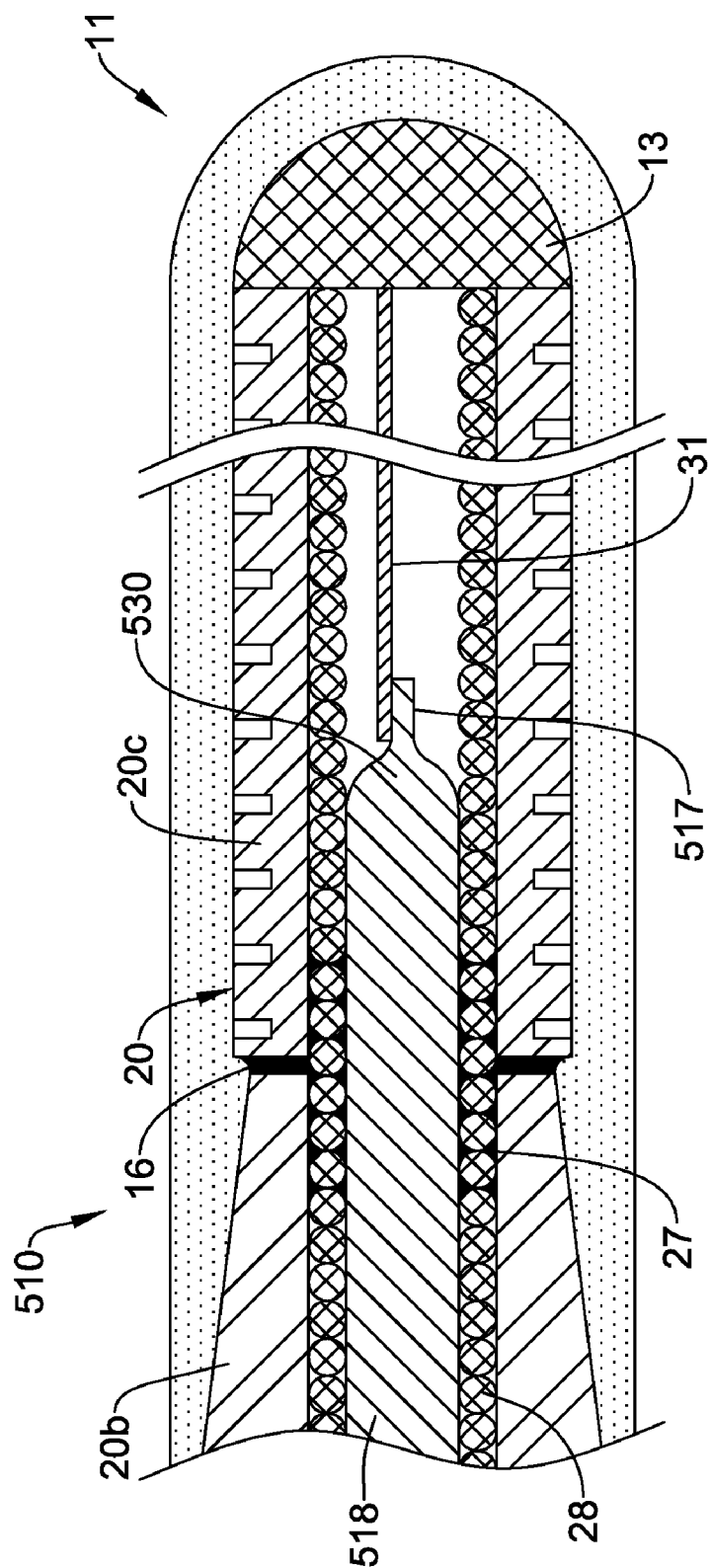
FIG. 8 is a cross-sectional side view of a portion of another example medical device.

FIG. 8 illustrates another example guidewire 510 that is similar in some respects to other devices disclosed herein, wherein like reference numbers indicate similar structure. In particular, this embodiment is somewhat similar to the guidewire 10 of FIG. 3, except that a different tip configuration is used. In this embodiment, the core wire 518 ends proximally from the distal tip 11, and includes a flattened distal section 517. A shaping structure, such as a shaping ribbon or wire 31 is attached to the core wire 518, for example at the flattened distal section 517, and extends to the distal tip 11, for example to the distal tip member 13.

Figure 9:
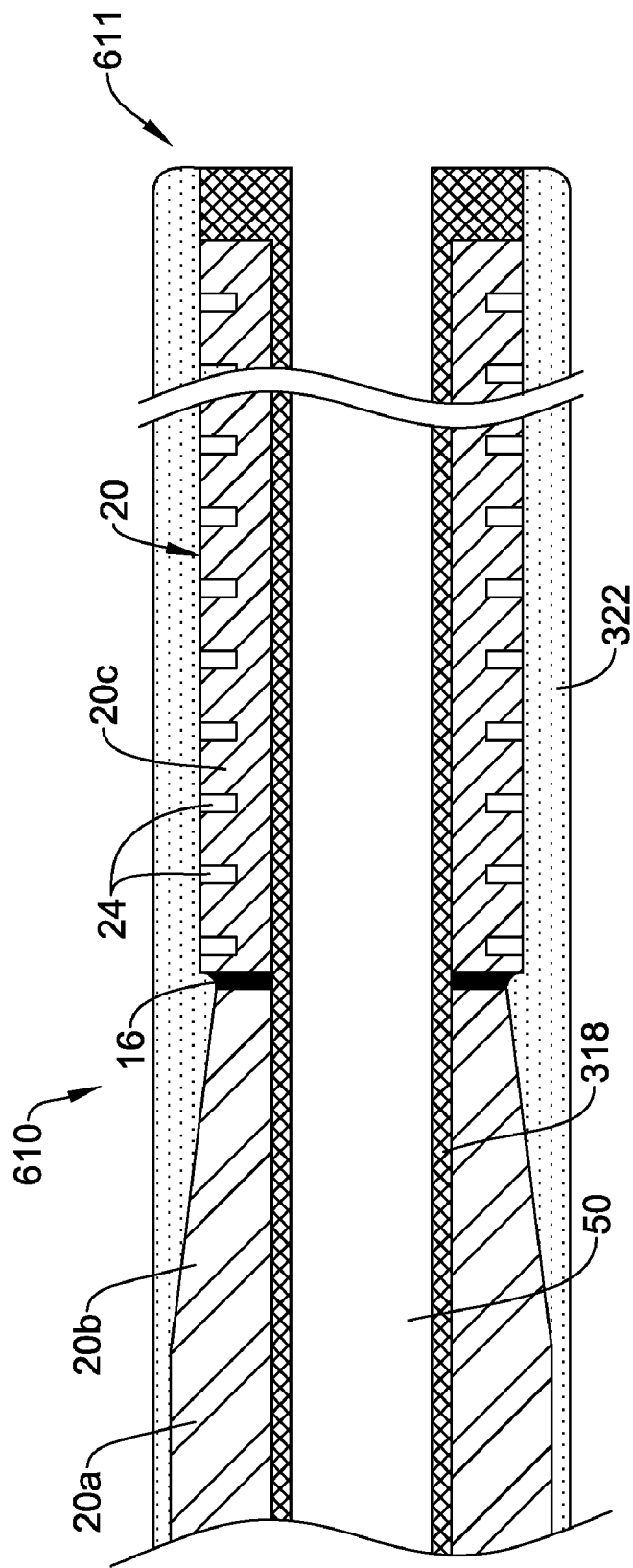
FIG. 9 is a cross-sectional side view of a portion of another example medical device.

While many of the embodiments discussed above relate to the use of such tubular members 20/120 in the construction of a guidewire, as indicated above, such members may also be used in other medical devices. In that regard, refer now to FIG. 9, which shows a medical device 610 which may, for example, be a catheter 610 including such a tubular member 20. The tubular member 20 can be similar in many respects to the tubular member 20 shown in FIG. 3, including a first section 20a, a tapered section 20b, and a slotted section 20c. Similar to the tubular member used in the guidewire in the embodiment shown in FIG. 3, the tubular member 20 in this embodiment may also be made of, or include, two or more discrete tubular members or components that are attached, joined or bonded together in a suitable manner, for example, tapered section 20b and slotted section 20c. In this case, rather than a core wire 18 as used in the guidewire embodiments discussed above, an inner member 318, such as sleeve or jacket of tubular material, may be disposed within the tubular member 20. The inner member 318 may functions as an inner tubular member 318 for the catheter 610, and may define a lumen 50 that may be adapted and/or configured to receive or transport other medical devices, fluids, medicaments, of the like. The inner member 318 may extend the length of the catheter 610, or may end at an appropriate location along the length of the catheter. The tubular member 20 and the inner tubular member 318 can be attached and/or constructed in a manner as discussed above, and/or can include or be made of materials such as many of those discussed above. For example, in some embodiments, the inner tubular member 318 may be made of a polymer material, such as PTFE or the like, and the tubular member 20 may be a nickel titanium alloy.

The catheter 610 may also include a sheath 322 of one or more outer layers and/or members disposed about the tubular member 20. The one or more outer layers and/or members 322 may be made of any suitable materials, including those discussed herein, and in some embodiments, may be one or more layers or polymer material. Some examples of suitable polymer materials can include those discussed above regarding the sheath 22, and may be disposed about the tubular member 20 in any suitable manner, including any of those discussed above. The catheter may also include a coating material, for example, a lubricious, a hydrophilic, a protective, or other type of coating may be applied over portions or all of sheath 322 and/or the tubular member 20. The tubular member 20 may also include a surface treatment, such as those discussed above. Some examples of suitable coating materials include those discussed above. The catheter 610 can include a distal tip section 611 that may be defined by a distal portion of the inner tubular member 28, the sheath 322, or both, extending distally beyond and/or partially about the distal end of the tubular member 20. In some embodiments, additional material, such as a softer or more flexible polymer material can be added to the tip to provide a more atraumatic tip.

Figure 10:
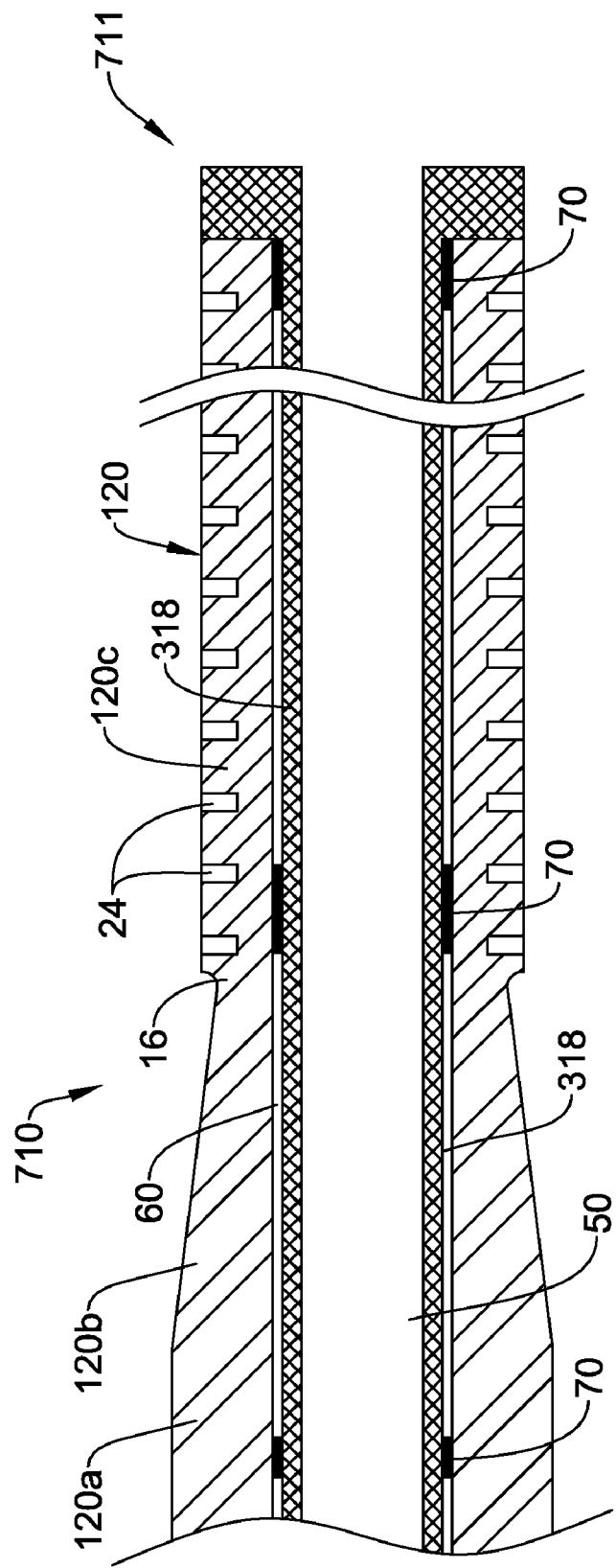
FIG. 10 is a cross-sectional side view of a portion of another example medical device.

FIG. 10 illustrates another example catheter 710 that is similar in many respects to the catheter 610. In this embodiment, however, the tubular member 120 is formed from a continuous or one-piece member that defines first section 120a, tapered section 120b, and slotted section 120c—similar to the tubular member 120 in the guidewire construction of FIG. 4. Additionally, as illustrated in this embodiment, the inner member 318 may be disposed within the tubular member 120 such that a space or gap 60 is defined between at least a portion of the inner surface of the tubular member 120 and the outer surface of the inner member 318. The inner member 318 may be attached to the tubular member 120 at discrete attachment points 70. Although not shown, the catheter 710 may also include a sheath 322, as discussed above regarding the embodiment shown in FIG. 9 and/or may include a coating or surface treatment, such as those discussed above. Again, the catheter 710 may include a distal tip portion 711 that may include a portion of the inner member 228 that extends distally beyond the tubular member 120, and/or may include additional material, such as softer or more flexible polymer material that would provide a desired tip. In still other embodiments, tubular member 120, as well as any of the other tubular members disclosed herein, may include one more sections with an interior taper such that the inner diameter of tubular member 120 increases and/or decreases along the length thereof. In these embodiments, the wall thickness of tubular member 120 may remain constant adjacent to (e.g., along) the interior taper or it may increase and/or decrease along the interior taper.

FIGS. 11-15 illustrate various additional embodiments of slotted sections appropriate for various embodiments of medical devices that may be at least somewhat distinct from those shown in the other figures. For ease in understanding, these figures depict various "slotted sections" of tubular members (e.g. 20 and 120) that are appropriate for numerous embodiments. For example, FIG. 11 illustrates slotted section 320c having slots 324. Slots 324 have the same shape and are arranged in a regular pattern. FIG. 12 illustrates another example slotted section 420c where slots 424 have an elongated rectangular shape and are arranged in a longitudinallyaligned pattern. FIG. 13 illustrates another example slotted section 520c having slots 524a and 524b that alternate between a longitudinally arrangement (i.e., slots 524a) and an axial or "vertical" arrangement (i.e., slots 524b). FIG. 14 illustrates another example slotted section 620c having slots 624 that are substantially round. FIG. 15 illustrates another example slotted section 720c having slots 724 that are arranges at an angle, and may spiral about a portion of slotted section 720c or are otherwise arranged in a helical manner. As can be appreciated by those of skill in the art and others, the slots described above may take any of a wide variety of shapes and/or forms, or combinations of shapes and forms. In at least some embodiments, the slots are adapted and/or configured to provide the tubular member in which they are defined an increased level of lateral flexibility relative to a similar tubular member not including such slots. In other embodiments, rather than slots, a single helical groove formed in a tubular member to modify the flexibility characteristics as desired.

It should be understood that this disclosure is, in many respects, only illustrative. Changes may be made in details, particularly in matters of shape, size, and arrangement of steps without exceeding the scope of the invention. In addition, many of the structures, material, or methods or combinations thereof described or shown in one or more embodiments may be incorporated into other embodiments as desired. The invention's scope is, of course, defined in the language in which the appended claims are expressed.

What is claimed is:

1. A medical device, comprising:
   an elongate inner member having a proximal section and a distal section;
   an elongated metallic tubular member disposed about the inner member, the tubular member including a first section, a tapered section, and a slotted section having a plurality of slots defined therein, wherein the tapered section is disposed between the first section and the slotted section; and
   wherein the elongated metallic tubular member includes a length and defines a lumen extending therethrough, the lumen having an inner diameter, and wherein the inner diameter of the lumen remains substantially constant along the length of the tubular member.

2. The medical device of claim 1, wherein the slotted section is more flexible than the first section and the tapered section includes flexibility characteristics that transition between the flexibility of the first section and the slotted section.

3. The medical device of claim 1, wherein the first section is free of slots formed therein.

4. The medical device of claim 1, wherein the tapered section is free of slots formed therein.

5. The medical device of claim 1, wherein the first section has a first outer diameter, and the tapered section has a tapered outer diameter that tapers to a reduced outer diameter relative to the first outer diameter.

6. The medical device of claim 5, wherein the slotted section has an outer diameter that is substantially the same as the first outer diameter.

7. The medical device of claim 1, wherein the metallic tubular member comprises a nickel-titanium alloy.

8. The medical device of claim 7, wherein the nickel-titanium alloy comprises a super-elastic nickel-titanium alloy.

9. The medical device of claim 7, wherein the nickel-titanium alloy comprises a non-super-elastic nickel-titanium alloy.

10. The medical device of claim 1, wherein the elongated metallic tubular member comprises a single monolith of material that defines the first section and the tapered section.

11. The medical device of claim 10, wherein the slotted section is a discrete section that is affixed to the single monolith of material.

12. The medical device of claim 1, wherein the elongated metallic tubular member comprises a single monolith of material that defines the tapered section and the slotted section.

13. The medical device of claim 12, wherein the first section is a discrete section that is affixed to the single monolith of material.

14. The medical device of claim 1, wherein the first, tapered, and slotted sections are each discrete tubular sections that are affixed together.

15. The medical device of claim 1, wherein the first section is a proximal section, and the slotted section is a distal section, and tapered section is disposed between the proximal and distal sections.

16. The medical device of claim 1, wherein inner member is a core wire.

17. The medical device of claim 1, wherein inner member is an elongated inner tubular member defining a lumen extending therethrough.

18. The medical device of claim 1, further comprising an intermediate member disposed between the inner member and the elongated metallic tubular member.

19. The medical device of claim 1, further comprising a sheath disposed over at least a portion of the elongated metallic tubular member.

20. A medical device, comprising:
    an elongate inner member having a proximal section and a distal section;
    an elongated metallic tubular member disposed about the inner member, the tubular member including a first section, a tapered section, and a slotted section having a plurality of slots defined therein, wherein the tapered section is disposed between the first section and the slotted section;
    wherein the elongated metallic tubular member comprises a single monolith of material that defines the first section and the tapered section; and
    wherein the single monolith of material also defines the slotted section.

21. A medical device, comprising:
    an elongate inner member having a proximal section and a distal section;
    an elongated metallic tubular member disposed about the inner member, the tubular member including a first section, a tapered section, and a slotted section having a plurality of slots defined therein, wherein the tapered section is disposed between the first section and the slotted section; and
    wherein inner member is an elongated inner tubular member defining a lumen extending therethrough; and
    wherein inner tubular member comprises a polymeric material.

22. A medical device, comprising:
    an elongate inner member having a proximal section and a distal section;
    an elongated metallic tubular member disposed about the inner member, the tubular member including a proximal section having a first lateral flexibility, a slotted distal section having a plurality of slots defined therein and having a second lateral flexibility that is greater than the first lateral flexibility, and means for providing a transition in flexibility characteristics between the proximal section and the slotted distal section; and wherein the elongated metallic tubular member includes a length and defines a lumen extending therethrough, the lumen having an inner diameter, and wherein the inner diameter of the lumen remains substantially constant along the length of the tubular member.

23. An elongate tubular component for use in a medical device, the tubular component comprising:

an elongated metallic tubular member defining a lumen extending therethrough, the metallic tubular member including:

a first section having a first degree of lateral flexibility;

a third section including a plurality of slots formed therein and having a second degree of lateral flexibility that is greater than the first degree lateral flexibility;

an intermediate section that is tapered and is disposed between and interconnects the first and third section, wherein the tapered intermediate section provides for flexibility characteristics that transition between the first and second degrees of lateral flexibility;

wherein the elongated metallic tubular member comprises a single monolith of material that defines the first section, the second intermediate section, and the third section.

24. The elongate tubular component of claim 23, wherein the first section is substantially free of slots formed therein.

25. The elongate tubular component of claim 23, wherein the intermediate section is free of slots formed therein.

26. The elongate tubular component of claim 23, wherein the first section has a first outer diameter, and the tapered section has a tapered outer diameter that tapers to a reduced outer diameter relative to the first outer diameter.

27. The elongate tubular component of claim 23, wherein the third section has an outer diameter that is substantially the same as the first outer diameter.

28. The elongate tubular component of claim 23, wherein the metallic material comprises a nickel-titanium alloy.

29. The elongated tubular component of claim 28, wherein the nickel-titanium alloy comprises a super-elastic nickel-titanium alloy.

30. The elongated tubular component of claim 28, wherein the nickel-titanium alloy comprises a non-super-elastic nickel-titanium alloy.

31. The elongate tubular component of claim 23, wherein the first section is a proximal section, and the third section is a distal section, and intermediate section is disposed between the proximal and distal sections.

* * * * *

UNITED STATES PATENT AND TRADEMARK OFFICE
CERTIFICATE OF CORRECTION

| | | |
|---|---|---|
| PATENT NO. | : 7,914,467 B2 | Page 1 of 1 |
| APPLICATION NO. | : 11/836039 | |
| DATED | : March 29, 2011 | |
| INVENTOR(S) | : Ted Layman et al. | |

It is certified that error appears in the above-identified patent and that said Letters Patent is hereby corrected as shown below:

Column 18
Line 2, delete "substantially".

Signed and Sealed this
Twenty-fourth Day of May, 2011

David J. Kappos
*Director of the United States Patent and Trademark Office*